(12) United States Patent
Taron et al.

(10) Patent No.: US 8,486,660 B2
(45) Date of Patent: *Jul. 16, 2013

(54) METHODS AND COMPOSITIONS FOR CONCENTRATING SECRETED RECOMBINANT PROTEIN

(75) Inventors: Christopher H. Taron, Essex, MA (US); Paul A. Colussi, Gloucester, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/346,258

(22) Filed: Jan. 9, 2012

(65) Prior Publication Data

US 2012/0107877 A1 May 3, 2012

Related U.S. Application Data

(60) Continuation of application No. 12/399,059, filed on Mar. 6, 2009, now Pat. No. 8,119,390, which is a division of application No. 11/242,553, filed on Oct. 3, 2005, now Pat. No. 7,517,671, which is a continuation-in-part of application No. 11/102,475, filed on Apr. 8, 2005, now Pat. No. 7,390,636, said application No. 11/242,553 is a continuation-in-part of application No. 11/110,001, filed on Apr. 20, 2005, now Pat. No. 6,984,505, which is a division of application No. 10/375,913, filed on Feb. 26, 2003, now Pat. No. 6,897,285, said application No. 11/242,553 is a continuation-in-part of application No. 11/110,002, filed on Apr. 20, 2005, now Pat. No. 6,987,007.

(60) Provisional application No. 60/560,418, filed on Apr. 8, 2004, provisional application No. 60/360,354, filed on Feb. 28, 2002, provisional application No. 60/690,470, filed on Jun. 14, 2005, provisional application No. 60/616,420, filed on Oct. 6, 2004.

(51) Int. Cl.
*C12P 21/02* (2006.01)

(52) U.S. Cl.
USPC .......................... 435/69.1; 435/483; 536/23.4

(58) Field of Classification Search
None
See application file for complete search history.

(56) References Cited

U.S. PATENT DOCUMENTS

| | | | |
|---|---|---|---|
| 4,859,596 A | 8/1989 | Hollenberg et al. | |
| 5,160,726 A | 11/1992 | Josephson et al. | |
| 5,217,891 A | 6/1993 | Brake et al. | |
| 5,258,502 A * | 11/1993 | Kuranda | 530/350 |
| 5,262,176 A | 11/1993 | Palmacci et al. | |
| 5,643,758 A | 7/1997 | Guan et al. | |
| 5,679,544 A | 10/1997 | Fleer et al. | |
| 5,876,988 A | 3/1999 | Selten et al. | |
| 6,051,431 A | 4/2000 | Selten et al. | |
| 6,197,545 B1 * | 3/2001 | Fang et al. | 435/69.1 |
| 6,265,186 B1 | 7/2001 | Swinkels et al. | |
| 6,548,285 B1 | 4/2003 | Swinkels et al. | |
| 6,602,682 B1 | 8/2003 | VanDenBerg et al. | |
| 6,897,285 B2 | 5/2005 | Xu et al. | |
| 6,897,286 B2 | 5/2005 | Jaspers et al. | |
| 6,987,007 B2 * | 1/2006 | Xu et al. | 435/69.7 |
| 2005/0196804 A1 | 9/2005 | Xu et al. | |
| 2005/0196841 A1 | 9/2005 | Xu et al. | |

FOREIGN PATENT DOCUMENTS

| | | |
|---|---|---|
| EP | 0361991 | 12/1999 |
| JP | 62151430 | 7/1987 |
| WO | 03/074660 | 9/2003 |
| WO | 2004053460 | 6/2004 |
| WO | 2005/100586 | 10/2005 |

OTHER PUBLICATIONS

Ferrandon, et al. Biochim. Biophys. Acta., 1621:31-40 (2003).
Kim, et al. Trans. Res., 12:475-484 (2003).
Lachance, M.A., The Yeasts (Fourth Edition), 36:227-247 (1998).
Dickson, et al, Yeast Genetic Engineering, 19-40 (1989).
Gibbs, et al, Ferns Yeast Research, Elsevier Science, Tokyo, NL. 4:6 573-577 (2004).
Rose, et al, Gene, 29:1-2 113-124 (1984).
Arakane, et al, Insect Biochem. Mol. Biol. 33:631-48 (2003).
Bergkamp, et al, Curr. Genet. 21:365-70 (1992).
Bernard, et al, Anal. Biochem. 327:278-283 (2004).
Bulik, et al, Eukaryot. Cell 2:886-900 (2003).
Carstens, et al, Trans. Res. 12:497-508 (2003).
Chen, et al, Nucl. Acids Res. 14:4471 (1986).
Colussi, et al, Applied and Environmental Microbiology 71:2862-2869 (2005).
Dujon, et al, Nature, 430:35-44 (2004).
Durrens, et al, Curr. Genet. 18:7 (1990).
Falcone, et al, Plasmids 15:248 (1986).
Hanahan, et al, Methods Enzymol. 204:63-113 (1991).
Hashimoto, et al, J. Bacteriol. 182:3045-3054 (2000).

(Continued)

*Primary Examiner* — Jim Ketter
(74) *Attorney, Agent, or Firm* — New England Biolabs, Inc; Harriet M. Strimpel

(57) ABSTRACT

Methods and compositions are described that relate to obtaining concentrated preparations of secreted recombinant proteins. These proteins are expressed in the form of fusion proteins with a chitin-binding domain (CBD). The fusion proteins are capable of being concentrated in the presence of chitin. Also described is: a shuttle vector that includes a modified LAC4 promoter; a chitinase-negative host cell; a CBD capable of eluting from chitin under non-denaturing conditions; and sterilized chitin, which can be optionally magnetized for facilitating recovery of recombinant protein.

13 Claims, 13 Drawing Sheets

OTHER PUBLICATIONS

Henrissat, B., "Classification of chitinases modules," in Chitin and Chitinases, et. P. Jolles and R.A.A. Muzzarelli, pub. Birkhauser Verlag: Basel, Switzerland (1999).
Henrissat, et al, Biochem. J. 293:781-788 (1993).
Hsieh, et al, Appl. Microbiol. Biotechnol. 4:411-416 (1989).
Ito, et al, Biosci. Biotechnol. Biochem. 67: 847-855 (2003).
Karube, et al, FEBS Letters 182:90 (1985).
Kuranda, et al, J. Bio. Chem. 266:19758-19767 (1991).
Letunic, et al, Nucl. Acids Res. 30:242-244 (2002).
Merzendorfer, et al, J. Exptl. Biol. 206:4393-4412 (2003).
Miller, J.F., Methods Enzymol. 235:375-385 (1994).
Muller, et al, Yeast 14:1267-1283 (1998).
Muzzarelli, et al, "Native, industrial and fossil chitiins," in Chitin and Chitinases, ed. P. Jolles and R.A.A. Muzzarelli, pub. Birkhauser Verlag: Basel, Switzerland (1999).
Nielson, et al, Protein Eng. 10:1-6 (1997).
Robertus, et al, "The structure and action of chitinasaes," in Chitin and Chitinases, ed. P. Jolles and R.A.A. Muzzarelli, pub. Birkhauser Verlag: Basel, Switzerland (1999).
Safarik, et al, Biomagnetic Research and Technology 2:7 (2004).
Safarik, et al, Journal of Biochemical and Biophysical Methods 27:327-330 (1993).
Schenborn, et al, Methods Mol Biol. 130:147-153 (2000).
Schenborn, et al, Methods Mol Biol. 130:155-164 (2000).
Schultz, et al, PNAS 95:5857-5864 (1998).
Strasser, et al, Eur. J. Biochem. 184:699-706 (1989).
van der Vlug-Bergmans, et al, Biotechnology Techniques 13:87-92 (1999).
Wang ,et al, Crit Rev Biotechnol. 21(3): 177-218 (2001).

* cited by examiner

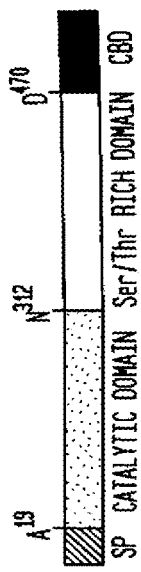

FAMILY 18 CHITINASE ACTIVE SITE

```
Consensus  [LIVMFY]-[DN]-G-[LIVFM]-[DN]-[LIVFM]-[DN]-X-E
                                                      158
             V150  D  G  F  D  F  D  I  E
KlCts1p
```

FIG. 2C

```
Consensus           --QDCTNALDGLYALGE------------CEP--QFLTCS------GGIARIMDCPADLIYNEP--LLICDWRHNVIGCEG
(SEQ ID NO:14)
KlCts1p             CS---DGEIS---------------CTADGKIAICN------YGAWYTECAAGTTCFA---YDSGDSVYTS--QNF
(SEQ ID NO:15)
C. fulvum           --TKCMGPKDCIYPNPD--------------SCT---TYIQCVPLDEVGNAKPVVKPCPKGLQWNDNVGKKWCDYPNLST-CPV
(SEQ ID NO:16)
R. solanacearum     --FKCP--APSGRYLVDDGTNNAGPNQVPRTNGTRA--YAVCD------AQSHATLDHCPSGQVFDK--RFSTCYVKD-A--CDE
(SEQ ID NO:17)
C. elegans          --FKCT--KDGFFGVPS------------DCL--KFIRCV------NGISYNFECPNGLSFHA--DTMMDDRPDPSK-CAK
(SEQ ID NO:18)
H. sapiens          --CAGRANGLYPVAN------------NRN--AFWHHCV------NGVTYQONCQAGLVFDT---SCDCCWWA-------
(SEQ ID NO:19)
D. melanogaster     --LECT--EGDYYPHR-----------NCR---KYYIC------NKALVPSEGGGDLHWDG--IKKLCDWPENVQ-CYT
(SEQ ID NO:20)
```

| | GROWTH TIME | | | |
|---|---|---|---|---|
| | 22 h | 44 h | 68 h | |
| WT | 768 | 798 | 763 | RFU min$^{-1}$ |
| ΔKlcts1 | 0 | 0 | 0 | |

← KlCts1p

SEQUENCE LISTING

```
<160> NUMBER OF SEQ ID NOS: 20

<210> SEQ ID NO 1
<211> LENGTH: 98
<212> TYPE: DNA
<213> ORGANISM: artificial
<220> FEATURE:
<223> OTHER INFORMATION: primer

<400> SEQUENCE: 1
ccagtaatgc aactatcaat cattgtgtta aactggtcac cagaaataca agatatcaaa      60
aattactaat actaccataa gccatcatca tatcgaag                             98

<210> SEQ ID NO 2
<211> LENGTH: 104
<212> TYPE: DNA
<213> ORGANISM: artificial
<220> FEATURE:
<223> OTHER INFORMATION: primer

<400> SEQUENCE: 2
ccaaactagc gtatccggtt ggattattgt tttcgatatc gaaatcgaaa ccatcgacga      60
cagcagtgtc gaatggtctt tccccggggt gggcgaagaa ctcc                      104

<210> SEQ ID NO 3
<211> LENGTH: 18
<212> TYPE: DNA
<213> ORGANISM: artificial
<220> FEATURE:
<223> OTHER INFORMATION: primer

<400> SEQUENCE: 3
gggcacaaca atggcagg                                                   18

<210> SEQ ID NO 4
<211> LENGTH: 19
<212> TYPE: DNA
<213> ORGANISM: artificial
<220> FEATURE:
<223> OTHER INFORMATION: primer

<400> SEQUENCE: 4
gcctctccac ccaagcggc                                                  19
```

```
<210> SEQ ID NO 5
<211> LENGTH: 36
<212> TYPE: DNA
<213> ORGANISM: artificial
<220> FEATURE:
<223> OTHER INFORMATION: primer

<400> SEQUENCE: 5
ggcggatccg ccaccatgtt tcaccctcgt ttactt                        36

<210> SEQ ID NO 6
<211> LENGTH: 34
<212> TYPE: DNA
<213> ORGANISM: artificial
<220> FEATURE:
<223> OTHER INFORMATION: primer

<400> SEQUENCE: 6
acatgcatgc ctagaagacg acgtcgggtt tcaa                          34

<210> SEQ ID NO 7
<211> LENGTH: 20
<212> TYPE: PRT
<213> ORGANISM: Kluyveromyces lactis

<400> SEQUENCE: 7

Phe Asp Ile Asn Ala Lys Asp Asn Val Ala Val Tyr Trp Gly Gln Ala
1               5                   10                  15

Ser Ala Ala Thr
            20

<210> SEQ ID NO 8
<211> LENGTH: 30
<212> TYPE: DNA
<213> ORGANISM: artificial
<220> FEATURE:
<223> OTHER INFORMATION: priimer

<400> SEQUENCE: 8
ggaagatctg actcctgggc tgttacaaga                               30

<210> SEQ ID NO 9
<211> LENGTH: 43
<212> TYPE: DNA
<213> ORGANISM: artificial
<220> FEATURE:
<223> OTHER INFORMATION: primer

<400> SEQUENCE: 9
ataagaatgc ggccgcctag aagacgacgt cgggtttcaa ata                43

<210> SEQ ID NO 10
<211> LENGTH: 39
<212> TYPE: DNA
<213> ORGANISM: artificial
<220> FEATURE:
<223> OTHER INFORMATION: primer

<400> SEQUENCE: 10
ccgctcgaga aaagagatgc acacaagagt gaggttgct                     39

<210> SEQ ID NO 11
<211> LENGTH: 33
<212> TYPE: DNA
<213> ORGANISM: artificial
<220> FEATURE:
<223> OTHER INFORMATION: primer
```

<400> SEQUENCE: 11
cgcggatcct aagcctaagg cagcttgact tgc                              33

<210> SEQ ID NO 12
<211> LENGTH: 33
<212> TYPE: DNA
<213> ORGANISM: artificial
<220> FEATURE:
<223> OTHER INFORMATION: primer

<400> SEQUENCE: 12
ggaagatcta cgacaaatcc tggtgtatcc gct                              33

<210> SEQ ID NO 13
<211> LENGTH: 43
<212> TYPE: DNA
<213> ORGANISM: artificial
<220> FEATURE:
<223> OTHER INFORMATION: primer

<400> SEQUENCE: 13
ataagaatgc ggccgcttat tgaagctgcc acaaggcagg aac                   43

<210> SEQ ID NO 14
<211> LENGTH: 57
<212> TYPE: PRT
<213> ORGANISM: artificial
<220> FEATURE:
<223> OTHER INFORMATION: Type 2 chitin-binding domain consensus sequence

<400> SEQUENCE: 14

Gln Asp Cys Thr Asn Ala Leu Asp Gly Leu Tyr Ala Leu Gly Glu Cys
1               5                   10                  15

Glu Pro Gln Phe Leu Thr Cys Ser Gly Gly Ile Ala Arg Ile Met Asp
            20                  25                  30

Cys Pro Ala Asp Leu Ile Tyr Asn Glu Pro Leu Leu Ile Cys Asp Trp
        35                  40                  45

Arg His Asn Val Ile Gly Cys Glu Gly
    50                  55

<210> SEQ ID NO 15
<211> LENGTH: 48
<212> TYPE: PRT
<213> ORGANISM: Kluyveromyces lactis

<400> SEQUENCE: 15

Cys Ser Asp Gly Glu Ile Ser Cys Thr Ala Asp Gly Lys Ile Ala Ile
1               5                   10                  15

Cys Asn Tyr Gly Ala Trp Val Tyr Thr Glu Cys Ala Ala Gly Thr Thr
            20                  25                  30

Cys Phe Ala Tyr Asp Ser Gly Asp Ser Val Tyr Thr Ser Cys Asn Phe
        35                  40                  45

<210> SEQ ID NO 16
<211> LENGTH: 64
<212> TYPE: PRT
<213> ORGANISM: Cladosporium fulvum

<400> SEQUENCE: 16

Thr Lys Cys Met Gly Pro Lys Asp Cys Leu Tyr Pro Asn Pro Asp Ser
1               5                   10                  15

Cys Thr Thr Tyr Ile Gln Cys Val Pro Leu Asp Glu Val Gly Asn Ala

```
                        20                  25                  30

Lys Pro Val Val Lys Pro Cys Pro Lys Gly Leu Gln Trp Asn Asp Asn
                35                  40                  45

Val Gly Lys Lys Trp Cys Asp Tyr Pro Asn Leu Ser Thr Cys Pro Val
         50                  55                  60

<210> SEQ ID NO 17
<211> LENGTH: 68
<212> TYPE: PRT
<213> ORGANISM: Ralstonia solanacearum

<400> SEQUENCE: 17

Phe Lys Cys Pro Ala Pro Ser Gly Arg Tyr Leu Val Asp Asp Gly Thr
1               5                   10                  15

Asn Asn Arg Gly Pro Asn Gln Val Pro Arg Thr Asn Cys Thr Arg Ala
                20                  25                  30

Tyr Ala Val Cys Asp Ala Gln Ser His Ala Thr Leu Asp His Cys Pro
            35                  40                  45

Ser Gly Gln Val Phe Asp Lys Arg Phe Ser Thr Cys Val Val Lys Asp
        50                  55                  60

Ala Cys Asp Glu
65

<210> SEQ ID NO 18
<211> LENGTH: 54
<212> TYPE: PRT
<213> ORGANISM: Caenorhabditis elegans

<400> SEQUENCE: 18

Phe Lys Cys Thr Lys Asp Gly Phe Phe Gly Val Pro Ser Asp Cys Leu
1               5                   10                  15

Lys Phe Ile Arg Cys Val Asn Gly Ile Ser Tyr Asn Phe Glu Cys Pro
                20                  25                  30

Asn Gly Leu Ser Phe His Ala Asp Thr Met Met Cys Asp Arg Pro Asp
            35                  40                  45

Pro Ser Lys Cys Ala Lys
        50

<210> SEQ ID NO 19
<211> LENGTH: 48
<212> TYPE: PRT
<213> ORGANISM: Homo sapiens

<400> SEQUENCE: 19

Cys Ala Gly Arg Ala Asn Gly Leu Tyr Pro Val Ala Asn Asn Arg Asn
1               5                   10                  15

Ala Phe Trp His His Cys Val Asn Gly Val Thr Tyr Gln Gln Asn Cys
                20                  25                  30

Gln Ala Gly Leu Val Phe Asp Thr Ser Cys Asp Cys Cys Asn Trp Ala
            35                  40                  45

<210> SEQ ID NO 20
<211> LENGTH: 52
<212> TYPE: PRT
<213> ORGANISM: Drosophila melanogaster

<400> SEQUENCE: 20

Leu Glu Cys Thr Glu Gly Asp Tyr Tyr Pro His Arg Asn Cys Arg Lys
1               5                   10                  15

Tyr Tyr Ile Cys Asn Lys Ala Leu Val Pro Ser Glu Cys Gly Gly Asp
```

-continued

```
                20               25               30
Leu His Trp Asp Gly Ile Lys Lys Leu Cys Asp Trp Pro Glu Asn Val
            35                  40              45
Gln Cys Val Thr
    50
```

METHODS AND COMPOSITIONS FOR CONCENTRATING SECRETED RECOMBINANT PROTEIN

CROSS REFERENCE

This application is a continuation of U.S. application Ser. No. 12/399,059 filed Mar. 6, 2009, which is a divisional of U.S. application Ser. No. 11/242,553 filed Oct. 3, 2005, which is a continuation-in-part of U.S. application Ser. No. 11/102,475 filed Apr. 8, 2005, which gains claims priority from Provisional Application Ser. No. 60/560,418 filed Apr. 8, 2004. U.S. application Ser. No. 11/242,553 filed Oct. 3, 2005 is also a continuation-in-part-of U.S. application Ser. Nos. 11/110,001 and Ser. No. 11/110,002 both filed Apr. 20, 2005 and both divisional applications of U.S. application Ser. No. 10/375,913 filed Feb. 26, 2003, now U.S. Pat. No. 6,897,285 issued May 24, 2005, which claims priority from Provisional Application Ser. No. 60/360,354 filed Feb. 28, 2002. U.S. application Ser. No. 11/242,553 filed Oct. 3, 2005 also claims priority from Provisional Application Ser. No. 60/616,420 filed Oct. 6, 2004 and Provisional Application Ser. No. 60/690,470 filed Jun. 14, 2005. Each of the above named applications are herein incorporated by reference.

BACKGROUND

Chitin, a β-1,4-linked un-branched polymer of N-acetylglucosamine (GlcNAc), constitutes the second most abundant polymer on earth following cellulose. It is a major component of insect exoskeletons (Merzendorfer, H., et al., *J. Exptl. Biol.* 206:4393-4412 (2003), the shells of invertebrate crustaceans and of fungal cell walls (Riccardo, A., et al. "Native, industrial and fossil chitins," in *Chitin and Chitinases*, ed. P. Jolles and R. A. A. Muzzarelli, pub. Birkhauser Verlag: Basel, Switzerland (1999)). Chitinases hydrolyze the β-1,4-glycosidic bond of chitin and have been found in prokaryotic, eukaryotic and viral organisms. In the yeast *Saccharomyces cerevisiae*, chitinase plays a morphological role in efficient cell separation (Kuranda, M., et al. *J. Biol. Chem.* 266:19758-19767 (1991)). Additionally, plants express chitinases in defense against chitin-containing pathogens. In fact, the heterologous expression of chitinase genes in transgenic plants has been shown to increase resistance to certain plant pathogens (Carstens, M., et al. *Trans. Res.* 12:497-508 (2003); Itoh, Y., et al. *Biosci. Biotechnol. Biochem.* 67:847-855 (2003); Kim, J. et al. *Trans. Res.* 12:475-484 (2003)). Chitinases belong to either family 18 or family 19 of glycosylhydrolases based on their amino acid sequence similarities (Henrissat, B., et al. *Biochem. J.* 293:781-788 (1993)). Familial differences in chitinase catalytic domain sequences reflect their different mechanisms of chitin hydrolysis that result in either retention (family 18) or inversion (family 19) of the anomeric configuration of the product (Robertus, J. D., et al. "The structure and action of chitinases," in *Chitin and Chitinases*, ed. P. Jolles and R. A. A. Muzzarelli, pub. Birkhauser Verlag: Basel, Switzerland (1999)).

Most chitinases have a modular domain organization with distinct catalytic and non-catalytic domains that function independently of each other. An O-glycosylated Ser/Thr-rich region often separates the two domains and may serve to prevent proteolysis or aid in secretion of the chitinase (Arakane, Y., Q. et al. *Insect Biochem. Mol. Biol.* 33:631-48 (2003)). Non-catalytic chitin binding domains (CBDs also referred to as ChBDs) belong to one of three structural classes (type 1, 2 or 3) based on protein sequence similarities (Henrissat, B. "Classification of chitinases modules," in *Chitin and Chitinases*, ed. P. Jolles and R. A. A. Muzzarelli, pub. Birkhauser Verlag Basel, Switzerland (1999)). Depending on the presence of a CBD can either enhance (Kuranda, M., et al. *J. Biol. Chem.* 266:19758-19767 (1991)) or inhibit (Hashimoto, M., et al. *J. Bacteriol.* 182:3045-3054 (2000)) chitin hydrolysis by the catalytic domain.

The small size (~5-7 kDa), substrate binding specificity and high avidity of CBDs for chitin has led to their utilization as affinity tags for immobilization of proteins to chitin surfaces (Bernard, M. P., et al. *Anal. Biochem.* 327:278-283 (2004); Ferrandon, S., et al. *Biochim. Biophys. Acta.* 1621:31-40 (2003)). For example, the *B. circulans* chitinase A1 type 3 CBD has been used to immobilize fusion proteins expressed in bacteria on chitin beads to provide a platform for intein-mediated protein splicing (Ferrandon, S., et al. *Biochim. Biophys. Acta.* 1621:31-40 (2003)) and to chitin-coated microtiter dishes (Bernard, M. P., et al. *Anal. Biochem.* 327:278-283 (2004)). Because eukayotic protein expression systems are capable of biological processes not possible with bacterial systems (e.g. protein glycosylation, chaperone-mediated protein folding etc.) it is also desirable to secrete CBD-tagged proteins from eukaryotic cells. However, many eukaryotic cells, especially fungi, secrete endogenous chitinases that complicate the immobilization of CBD-tagged proteins to chitin by competing with the CBD-tagged protein for chitin-binding sites, by co-purifying with the CBD-tagged protein during chitin immobilization applications, and by degrading the target chitin-coated surface.

Proteins secreted from host cells into the surrounding media are substantially diluted resulting in a costly and cumbersome purification from large volumes. It is desirable to reduce the cost and increase the ease of separating proteins from the media in which they are secreted.

A variety of approaches exist to purify proteins from large volumes of media. These approaches vary in cost, efficiency and length of time required to achieve purification. For example, proteins in secreted culture can be harvested by precipitation. This approach requires addition of large quantities of a precipitating agent such as ammonium sulfate, acetone, or trichloroacetic acid, followed by centrifugation or filtration. Many of these agents are toxic or volatile, and all add significant expense to protein harvesting. Additionally, precipitation can result in significant loss of protein function.

Another approach is chromatography using various resins such as anion/cation exchange resins, hydrophobic interaction resins, or size exclusion gels. Harvesting proteins by chromatography requires that all of the spent culture medium be passed through the resin at a slow flow rate (typically, 1-10 ml min$^{-1}$). This can be very time-consuming in instances where large volumes of medium must be processed. For example, 100 liters of spent culture medium passed through a resin at a 5 ml min$^{-1}$ flow rate would take 333 hours to process. Additionally, these types of chromatography resins do not selectively purify only the target protein and must often be used in conjunction with other methods in a multi-step purification process.

Affinity chromatography resins that specifically bind peptide sequences incorporated into the protein's structure are often used because of their ability to selectively purify a target protein. In a typical strategy, a peptide sequence (e.g. a peptide antibody epitope or hexahistidine sequence) is engineered into the desired protein's sequence. A protein expressed with one of these tags will specifically interact with a corresponding resin (e.g. a resin having an immobilized antibody or a nickel resin for hexahistidine binding). While these methods often produce highly purified proteins from small volumes, they are limited in their practicality for processing large volumes by their cost and performance. For example, antibody affinity resins are very expensive and nickel resins can result in co-purification of undesired proteins that happen to contain stretches of histidine residues.

Magnetic techniques using magnetic carriers including beads have been used to purify proteins from cultures (Safarik et al. *Biomagnetic Research and Technology* 2:7 (2004)). A problem with this approach has been the need to customize each magnetic bead reagent to bind individual secreted proteins. This may involve complex chemistry to attach the affinity ligands to the beads. This also represents hurdles in efficiency and cost.

In some cases, natural affinities between the secreted protein and a substrate have been exploited. For example, lysozyme has a binding affinity for chitin so that when the hen egg white enzyme is exposed to chitin, it can be purified (Safarik et al. *Journal of Biochemical and Biophysical Methods* 27:327-330 (1993)).

SUMMARY

In one embodiment of the invention, a method is provided for obtaining a concentrated preparation of a secreted recombinant protein, that includes the steps of: (a) transforming host expression cells with a vector containing a DNA, the DNA encoding a fusion protein comprising a CBD and a target protein; (b) expressing the fusion protein in the host expression cells and secreting the fusion protein therefrom; and (c) binding the secreted fusion protein to a preparation of chitin by means of the CBD, the fusion protein being capable of elution into a desired buffer volume under non-denaturing conditions so as to obtain the concentrated preparation of the secreted recombinant protein.

In another embodiment of the invention, a method for obtaining a concentrated preparation of a secreted recombinant protein is provided which involves the steps of: (a) providing a shuttle vector, wherein the shuttle vector (i) a plasmid in *E. coli* and integrated into the genome of a yeast expression cell, and (ii) contains a DNA, the DNA encoding a fusion protein comprising a CBD and a target protein; (b) transforming a chitinase-deficient host expression cell with the shuttle vector for expressing the fusion protein in the yeast expression cell and secreting the fusion protein therefrom; and (c) binding the secreted fusion protein to a preparation of chitin by means of the CBD so as to obtain the concentrated preparation of secreted protein.

Both embodiments are exemplified using a shuttle vector, which in certain embodiments is capable of being cloned but not expressed in *E. coli* and is capable of expression in the host expression cells. An example of this type of shuttle vector is that which contains a modified LAC4 promoter and is further exemplified by pKLAC1.

Both embodiments are also exemplified using a host expression cell that is chitinase-deficient. The host expression system may be yeast cells, for example, a single yeast species selected from a *Kluyveromyces*, a *Yarrowia*, a *Pichia*, a *Hansenula*, and a *Saccharomyces* species. Where the yeast cells are a *Kluyveromyces* species, they may be selected from *Kluyveromyces marxianus* variety *fragilis* or *lactis*.

In examples of the above embodiments, chitin may be added to yeast cells in the culture medium during cultivation or at the end of the cultivation. Where further cultivation occurs, the chitin should be sterile. The chitin may be a coating, a colloid, a bead, a column, a matrix, a sheet or a membrane. Where the chitin is a bead, the bead may be either porous or non-porous. Optionally the chitin bead may be magnetized.

The fusion protein may be recovered when bound to magnetized chitin by applying a magnetic force. The binding of the fusion protein to chitin is optionally reversible such that the fusion protein can be released from the chitin under non-denaturing conditions that differ from the conditions for binding.

In an embodiment of the invention, a preparation of *Kluyveromyces* cells is characterized by a chitinase-negative phenotype wherein the phenotype is the result of a mutation in the chitinase gene expressing secreted chitinase, the preparation being capable of growing to a similar cell density as wild-type *Kluyveromyces* cells. The cell density refers to the dry weight of cells at 48 hours of cultivation (Colussi et al. *Applied and Environmental Microbiology* 71:2862-2869 (2005)).

Preferably, the preparation of *Kluyveromyces* cells is capable of expressing and secreting a recombinant fusion protein. Expression may be regulated by a LAC4 promoter or modification thereof, for example, using a shuttle vector having a modified LAC4 promoter for expressing a protein in *Kluyveromyces* while expressing substantially no protein in *E. coli*. An example of the shuttle vector is pKLAC1.

The preparation of *Kluyveromyces* cells described above may include a culture medium in which the *Kluyveromyces* is capable of at least one of growth and maintenance. The culture medium may also include sterilized chitin. The sterilized chitin may be in the form of magnetic beads capable of binding to a magnet placed within the culture medium or in contact with the vessel containing the culture medium.

LIST OF FIGURES

FIG. 1 shows a Western blot in which three proteins that are secreted by *K. lactis* into spent culture medium with approximate masses of >200, 85 and 50 kDa are cross-reacted with a polyclonal antibody raised against *B. circulans* Chi1A chitin-binding domain (α-CBD) (lane 1). The 85 kDa protein binds to chitin beads and corresponds to *K. lactis* chitinase (lane 2).

FIG. 2(A) shows a multi-domain KlCts1p chitinase with a signal peptide (stripes), a catalytic domain (gray), a Ser/Thr rich domain (white) and a chitin-binding domain (black). Signal peptide cleavage occurs after $A^{19}$.

FIG. 2(B) shows that KlCts1p belongs to Family 18 of glycosylhydrolases. The predicted catalytic site of KlCts1p lies between amino acids 150-158. Alternative amino acids for each of the 9 positions are provided in brackets. ("X" represents any amino acid.)

FIG. 2(C) shows that KlCts1p contains a type 2 chitin-binding domain. The KlCts1p CBD was aligned with a type 2 CBD consensus sequence (SEQ ID NO:14) predicted by SMART (Simple Modular Architecture Research Tool) software (Letunic, I., et al. *Nucl. Acids Res.* 30:242-244 (2002); Schultz, J., et al. *PNAS* 95:5857-5864 (1998)). Shown is the alignment of the KlCts1p CBD (SEQ ID NO:15) with example proteins containing predicted type 2 CBDs from fungi (*Cladosporium fulvum* (SEQ ID NO:16); Race-specific elicitor A4 precursor), bacteria (*Ralsonia solanacearum* (SEQ ID NO:17); Q8XZL0), nematodes (*Caenorhabditis elegans* (SEQ ID NO:18); probable endochitinase), mammals (*Homo sapiens* (SEQ ID NO:19); chitinase) and insects (*Drosophila melanogaster* (SEQ ID NO:20); probable chitinase 3). Conserved cysteine residues are indicated in bold print.

FIG. 3(A) shows chitinase activity measured following growth of cells for 22, 44 and 68 hours in YPD medium at 30°

C. Activity was assayed as the rate of release of 4-MU min$^{-1}$ (relative fluorescence units, RFU min$^{-1}$) from 50 mM 4MU-GlcNAc$_3$ at pH 4.5 and 37° C.

Figures 3A, 3B:
FIGS. 3A and 3B show that the deletion mutant of *K. lactis* does not secrete KlCts1p as determined by chitinase activity.

FIG. 3(B) shows that no secreted chitinase could be detected on a Western blot from the sample corresponding to the deletion mutant (lane 1) whereas chitinase was readily detected for the wild type (lane 2).

Figure 4A:
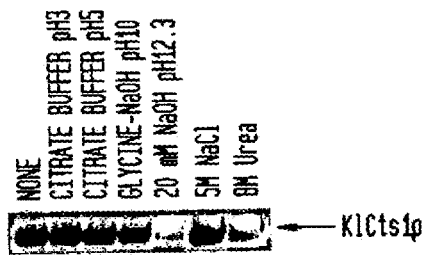

FIG. 4(A) shows the presence of secreted chitinase from *K. lactis* (KlCts1p) on Western Blots using α-CBD antibody. This assay required that the secreted chitinase be bound to a chitin column and then eluted in buffers of varying pH or by boiling for 2 minutes.

Figure 4B:
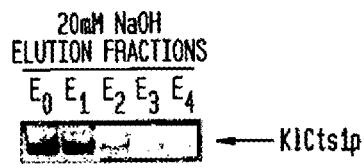

FIG. 4(B) shows that elution of chitinase (KlCts1p) from chitin occurs almost immediately with 20 mM NaOH. Chitin-bound KlCts1p was eluted in five successive 1 ml fractions of 20 mM NaOH (E$_0$-E$_4$ where E$_0$ represents the column void volume), separated by SDS-PAGE and detected by α-CBD Western blotting.

Figure 4C:
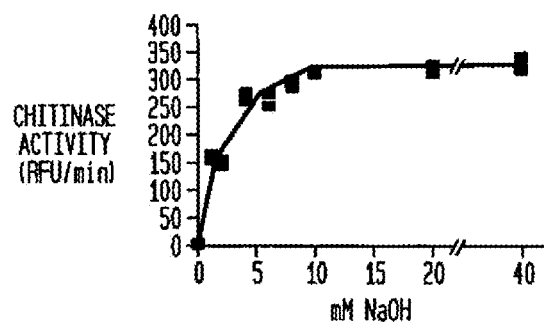

FIG. 4(C) shows that KlCts1p that has been eluted in 20 mM NaOH retains chitinolytic activity. Chitin-bound KlCts1p was eluted from chitin minicolumns with various concentrations of NaOH and the eluates assayed for chitinase activity by measuring the rate of release of 4-MU min$^{-1}$ from 50 mM 4MU-GlcNAc$_3$ at pH 4.5 and 37° C.

Figure 4D:
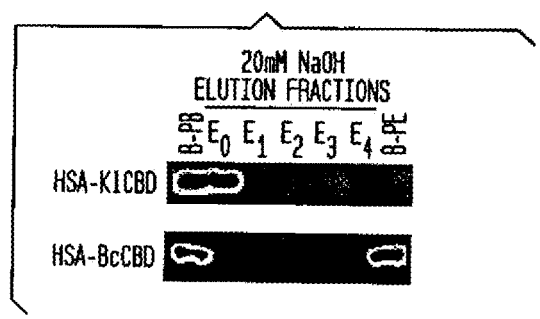

FIG. 4(D) shows that native KlCBD can function alone or as part of a fusion protein as an elutable affinity tag where the CBD is obtained from *K. lactis*, the fusion protein (Human serum albumin (HSA)-KlCBD) is expressed in a chitinase deficient *K. lactis* mutant (*K. lactis* Δcts1 cells) and the conditions for elution from chitin beads are 20 mM NaOH. In contrast, a fusion protein of CBD from *B. irculans* (HSA-BcCBD) is not similarly elutable from chitin beads in 20 mM NaOH. The control (B-PB) is fusion protein eluted by boiling chitin beads.

Figure 5:
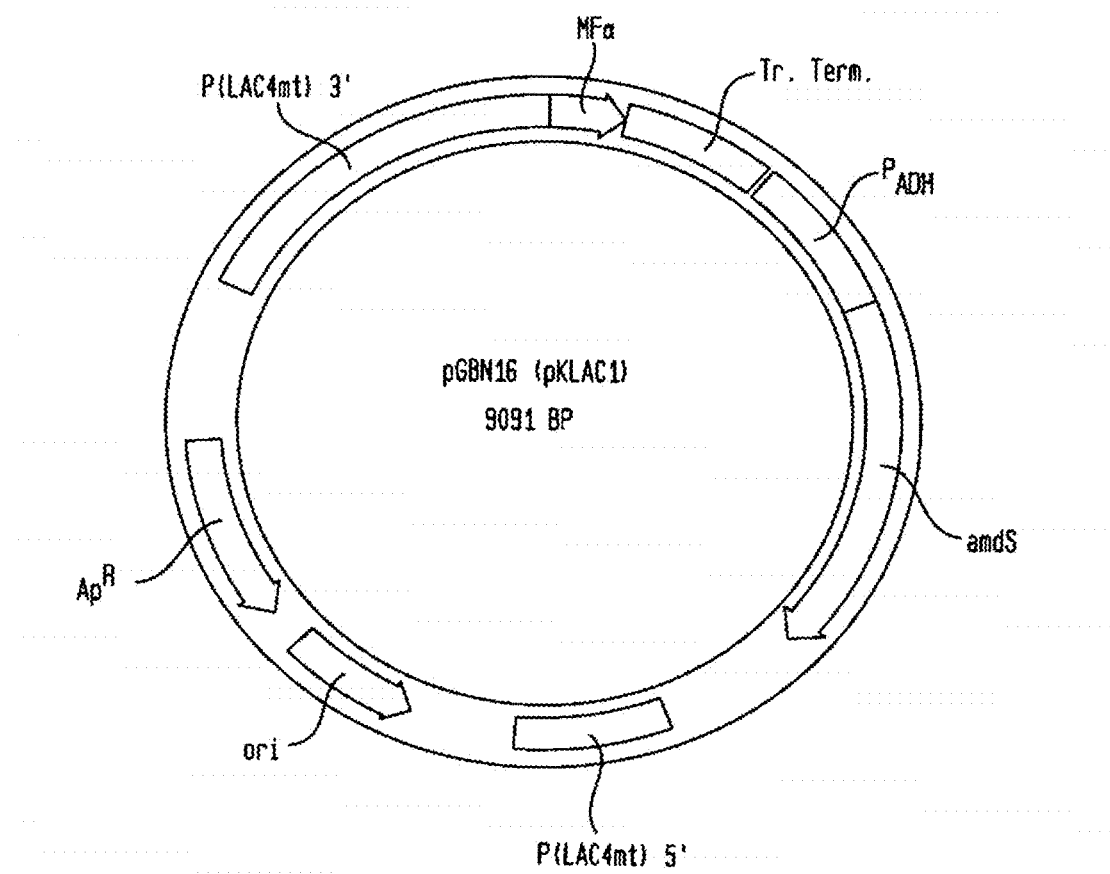

FIG. 5 shows the pGBN16 (pKLAC1) expression vector. The desired gene is cloned in the same translational reading frame as the mating factor alpha pre-pro secretion leader sequence that resides in the vector. A polylinker containing unique restriction sites is present to allow cloning of the desired gene.

Figure 6A:
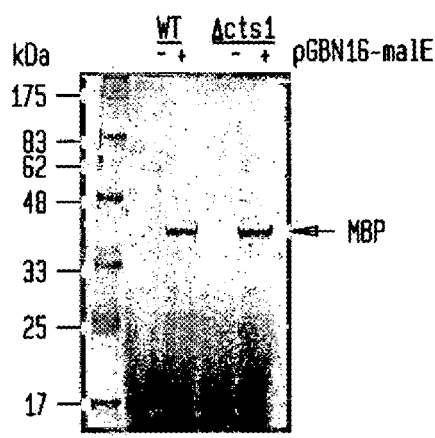
Figure 6B:

FIGS. 6A and 6B show secretion of recombinant proteins from *K. lactis* Δcts1 cells.

FIG. 6(A) shows secretion of maltose-binding protein (MBP) from Δcts1 *K. lactis* cells showing yields that are as good or better than from wild-type cells.

FIG. 6(B) shows secretion of an HSA-KlCBD fusion protein from Δcts1 *K. lactis* cells and elution of the fusion protein from chitin in 20 mM NaOH.

Figure 7:
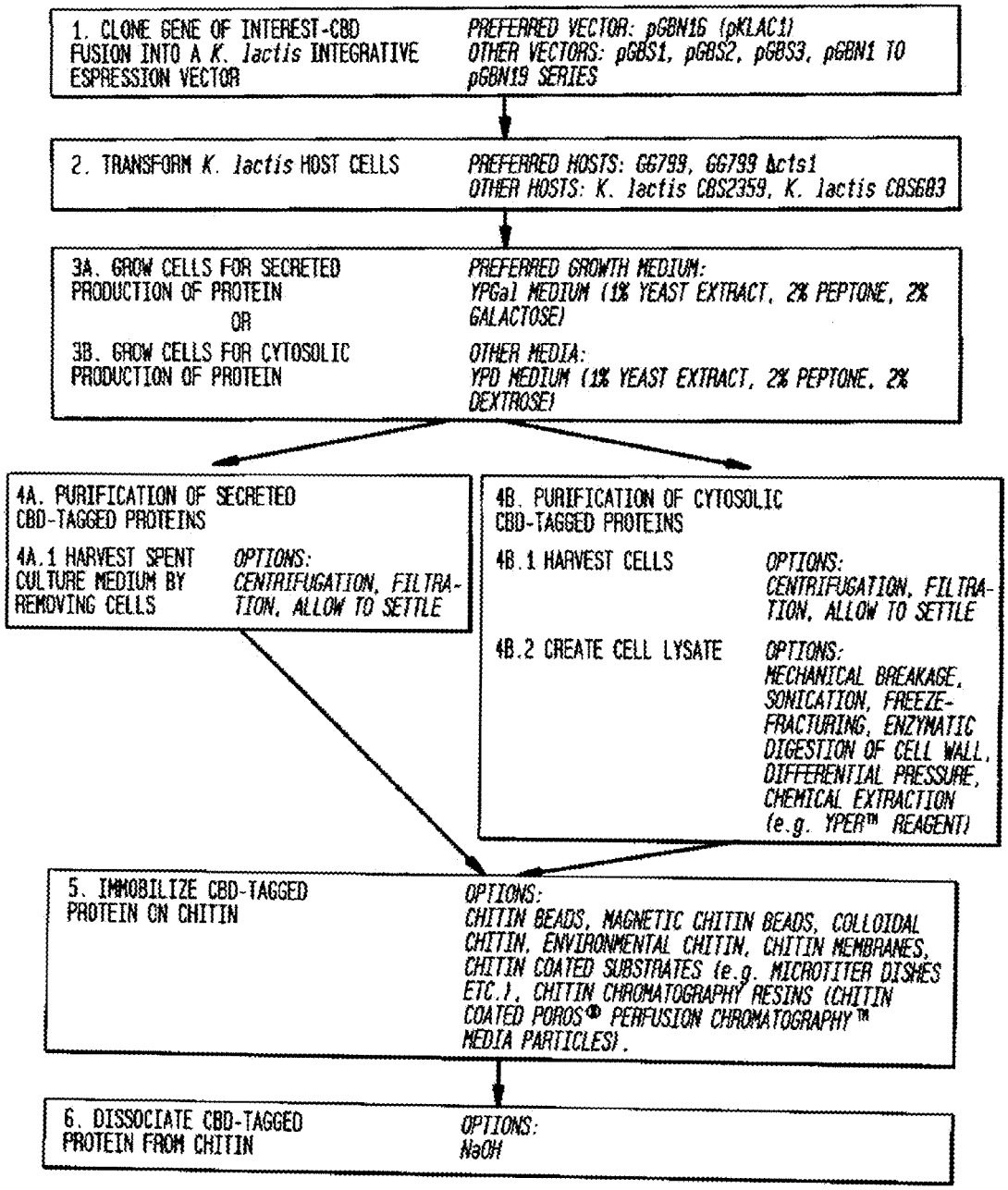

FIG. 7 is a flow diagram outlining secretion of CBD-tagged proteins from *K. lactis* cells.

Figure 8:
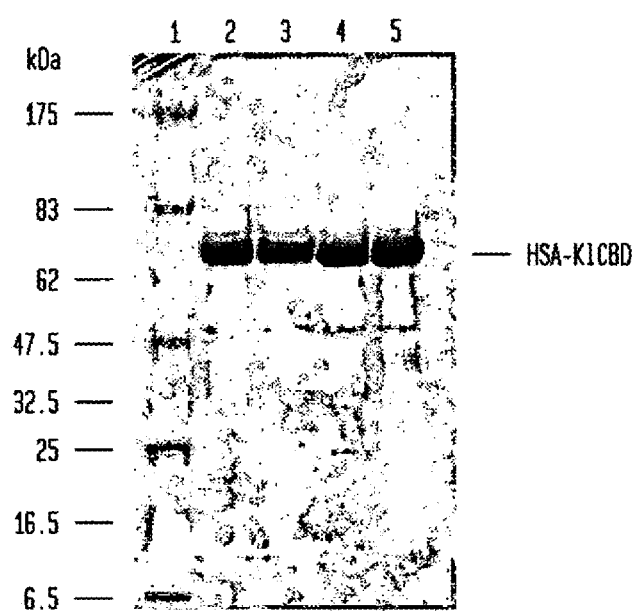

FIG. 8 shows SDS-PAGE separation of CBD-tagged human serum albumin (HSA-CBD) isolated from cultures using magnetic chitin beads added to the growth medium at various points of culture growth.

Lane 1 shows molecular weight markers.

Lane 2 shows HSA-KlCBD obtained from autoclave sterilized chitin magnetic beads that had been added as a media component to the *K. lactis* culture for 72 hours.

Lane 3 shows HSA-KlCBD obtained from autoclave sterilized chitin magnetic beads that had been added to a *K. lactis* culture for 48 hours.

Lane 4 shows HSA-KlCBD obtained from chitin magnetic beads added to the *K. lactis* culture one hour before harvesting.

Lane 5 shows HSA-KlCBD obtained from magnetic chitin beads added to supernatent from cell culture.

Figure 9A:
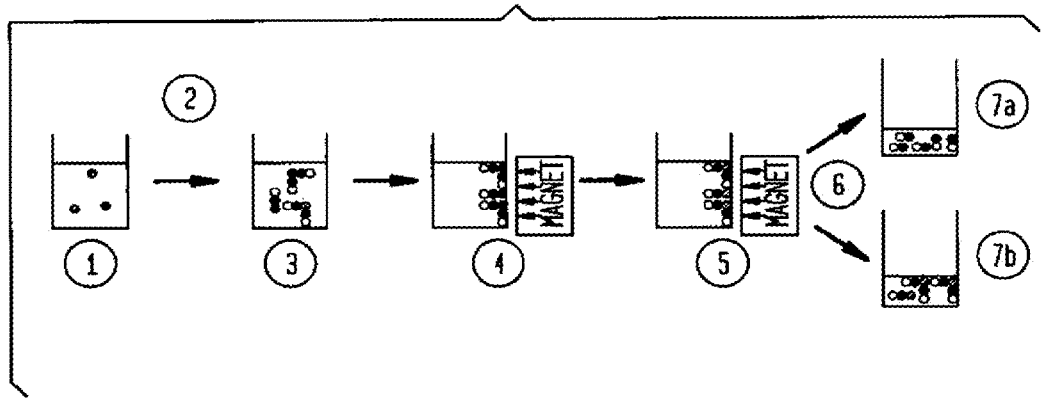
Figure 9B:
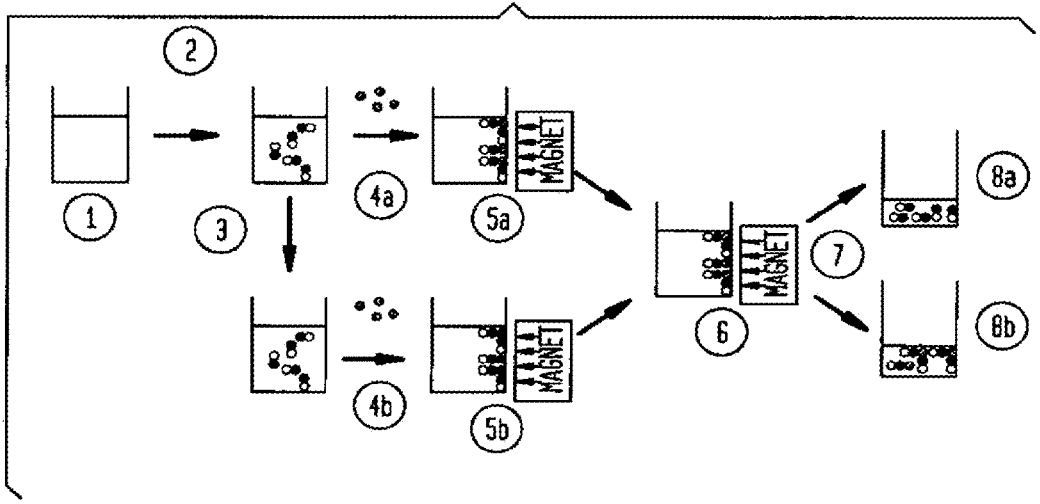
Figure 10A:
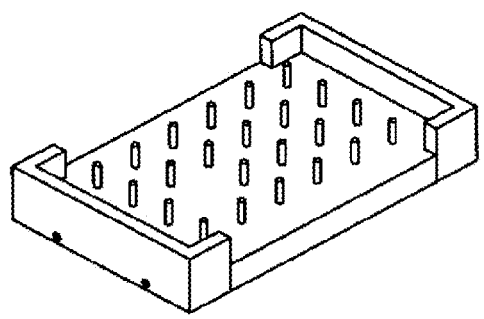
Figure 10B:
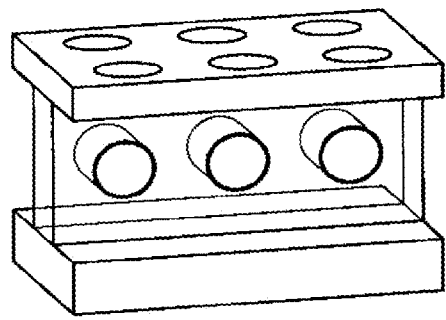
Figure 10C:
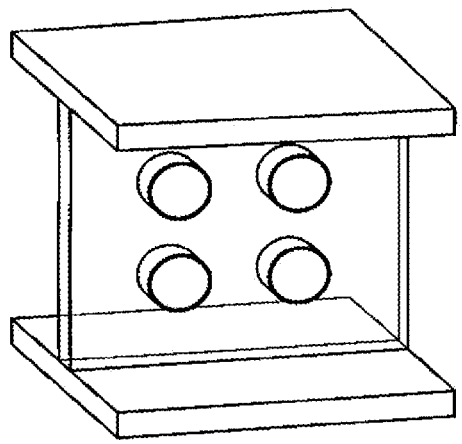
Figure 10D:
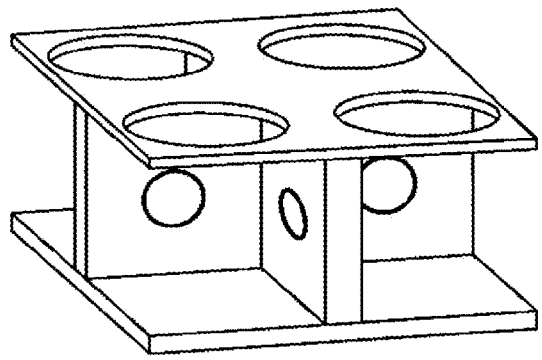

FIGS. 9A and 9B show a cartoon of how chitin magnetic beads can be used to purify proteins from a dilute solution.

FIG. 9A

Step 1: Magnetic chitin beads are sterilized (e.g. autoclaving, ultraviolet light, irradiation, chemical treatment, etc.).

Step 2: Sterilized chitin beads are added to growth medium prior to inoculation of the medium with cells. During growth of the cell culture the cells secrete proteins (open circles) that are tagged with a chitin-binding domain (black circles).

Step 3: Secreted CBD-tagged proteins become immobilized to the magnetic chitin beads in the growth medium.

Step 4: At some point during the growth of the culture, magnetic chitin beads containing bound CBD-tagged proteins are separated from cells and growth medium by exposure to a magnetic field to immobilize the beads.

Step 5: Beads are washed with a desired buffer or medium.

Step 6: The chitin bead-protein complexes are released from the magnetic field.

Step 7a: If a CBD that can be dissociated from chitin is used in construction of the fusion protein, purified CBD fusion proteins are eluted from the magnetic chitin beads.

Step 7b: Depending upon the desired application, harvested proteins remain immobilized on the chitin magnetic beads indefinitely.

FIG. 9B

Step 1: culture medium lacking magnetic chitin beads is inoculated with cells.

Step 2: Growing cells secrete proteins (open circles) that are tagged with a chitin-binding domain (black circles).

Step 3: The culture can be cleared of cells (e.g. centrifugation, filtration, flocculation, allowing cells to settle by gravity, etc and Step 4a: At any point during the growth of the culture, sterile magnetic chitin beads can be added directly to the culture Step 4b: Magnetic chitin beads added to the cleared spent culture medium.

Steps 5a and 5b: CBD-tagged proteins are separated from cells and/or growth medium by exposure to a magnetic field to immobilize the beads.

Step 6: Beads are washed with a desired buffer or medium.

Step 7: Release the chitin bead-protein complexes from the magnetic field.

Step 8a: If a CBD that can be dissociated from chitin is used in construction of the fusion protein, purified proteins are eluted from the magnetic chitin beads.

Step 8b: Depending upon the desired application, harvested proteins remain immobilized on the chitin magnetic beads indefinitely.

FIG. 10(*a*) shows a magnetic rack suitable for separating magnetic beads from a preparation in a microtiter dish.

FIG. 10(*b*) shows a magnetic rack suitable for separating magnetic beads from a preparation in a microcentrifuge tube.

FIG. 10(*c*) shows a magnetic rack suitable for separating magnetic beads from a preparation in a standard 50 ml laboratory tube.

FIG. 10(*d*) shows a magnetic rack suitable for separating magnetic beads from a preparation in a standard 250 ml centrifuge bottle.

Figure 11A:
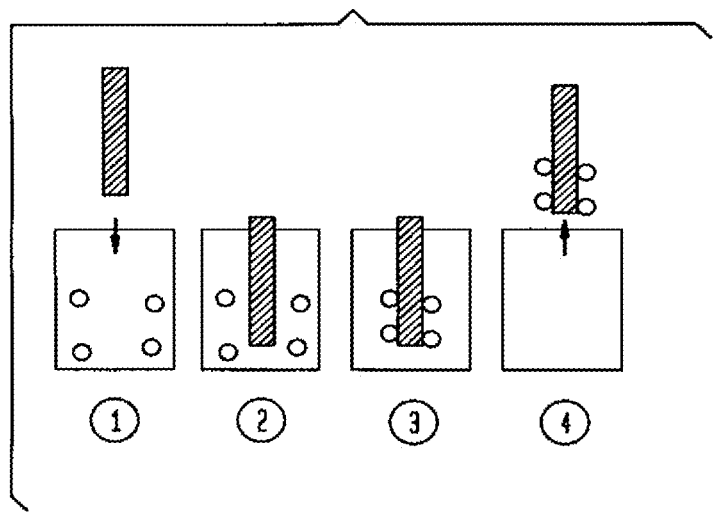

FIG. 11(*a*) shows a diagram of a submersible electromagnet probe suitable for separating magnetic beads from a preparation in a growth vessel or fermentor.

Steps 1 and 2: An electromagnet probe (dark gray) is submersed into a growth vessel or fermentor containing proteins immobilized to magnetic beads (gray).

Step 3: The electromagnet is turned on and the magnetic beads become immobilized on its surface.

Step 4: The electromagnet (turned on) is removed from the growth vessel or fermentor thereby isolating the magnetic beads.

Figure 11B:
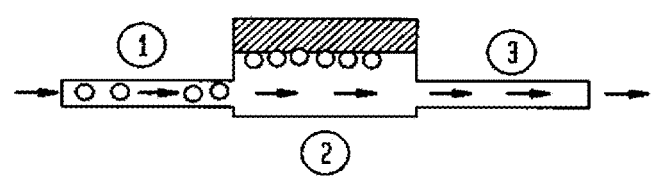

FIG. 11(b) shows a diagram of a magnetic device suitable isolating magnetic beads from the effluent of a fermentor or growth vessel.

Step 1: Effluent from a fermentor or vessel containing media, cells and proteins bound to magnetic beads (gray) flows from the fermentor into or through a magnetic isolation device.

Step 2: The magnetic isolation device consisting of an electromagnet or a removable permenant magnet separates the magnetic beads from the remaining effluent.

Step 3: The cleared effluent flows past the magnetic separation device.

Figure 12:
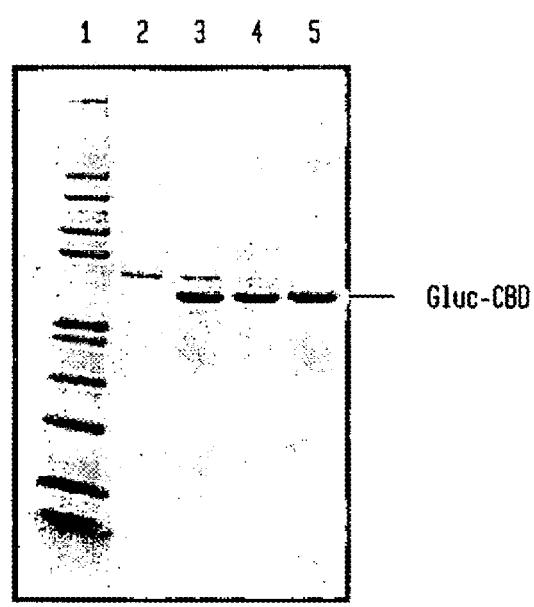

FIG. 12 shows that secreted GluC-CBD fusion protein from *Bacillus circulans* can be obtained regardless of whether magnetized chitin beads are added at the beginning or during cultivation of the cells or after the culture supernatent has been harvested. The gel shows amounts of GluC-CBD that were obtained after elution from magnetized chitin beads by boiling in SDS sample buffer.

Lane 1: Control—unstained standard (Mark 12—Invitrogen, Carlsbad, Calif.);

Lane 2: Control—GluC protein;

Lane 3: Overnight incubation of GluC-CBD transformed *B. circulans* cells. Magnetized chitin beads were added to the culture medium at the start of incubation;

Lane 4: Overnight incubation of GluC-CBD transformed *B. circulans* cells. Magnetized chitin beads were added to the culture medium 1 hr before collection of the medium;

Lane 5: Overnight incubation of GluC-CBD transformed *B. circulans* cells. Magnetized chitin beads were added to the supernatent after harvesting and centrifugation of the culture medium.

Figure 13:
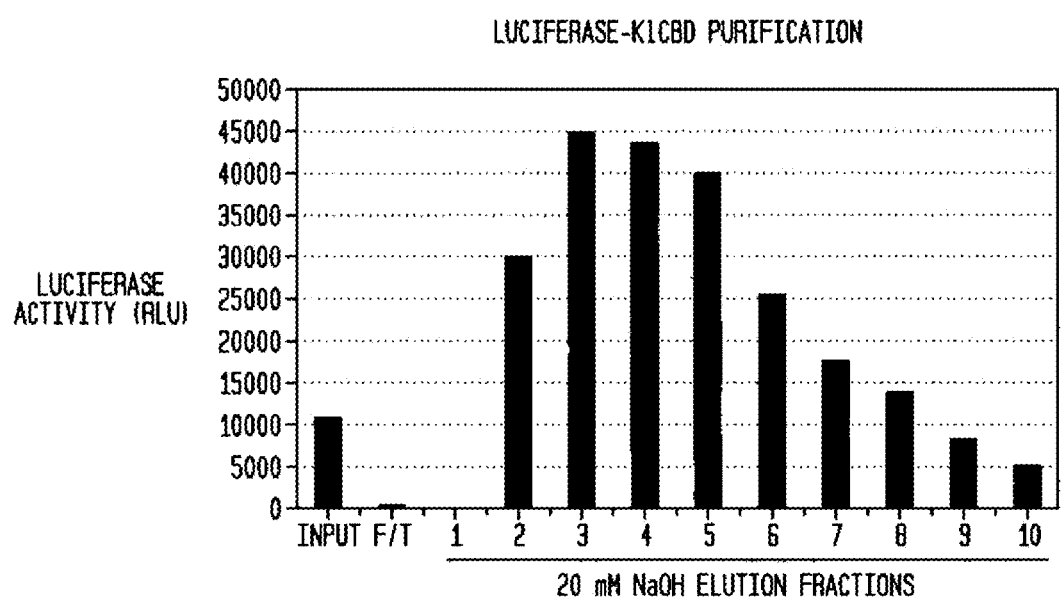

FIG. 13 shows a histogram in which amounts of luciferase obtained in a series of fractions from a chitin column reveal that luciferase-CBD was eluted in non-denaturing conditions in fractions 2 to 10 with the highest activity found in fractions 3, 4 and 5.

DETAILED DESCRIPTION

A process is described herein for concentrating proteins after their secretion into culture medium from the host cells in which the proteins are made. The process utilizes the binding affinity of CBD for chitin and can be enhanced by using cells that do not secrete chitinase. Chitinase-negative cells can be made as a result of a genetic modification or may occur naturally. It is desirable that these chitinase-deficient modified cells can be grown to similar density and at comparable yields as wild-type cells. The host cell can be transformed with a vector encoding a target gene fused to DNA expressing a CBD under a suitable promoter such that relatively large amounts of the target protein are secreted into production media by the host cell. The chitin substrate may be present in the production medium or in a separate reaction vessel for pulling the target protein out of a mixture. Binding of the CBD fusion protein concentrates the secreted recombinant protein on the surface of the chitin. The protein can be concentrated further using any of a number of approaches. For example, in one embodiment, the chitin is magnetized and a magnetic field is applied to the production medium, concentrating the chitin beads adjacent to a magnetic surface. Other embodiments include precipitation of chitin beads by centrifugation. The target protein can then be recovered from the concentrated chitin substrate.

The term "concentrated" refers to a ratio of weight to volume that after a procedure has been executed is greater than before the procedure.

Modification of Host Cells to Knock Out Chitinase Expression

The preferred host cell background for secretion of recombinant CBD-tagged proteins is one that: (i) produces no chitin-binding proteins or chitinolytic activity that would contaminate preparations of secreted fusion proteins that contain CBD; (ii) is capable of achieving high cell density in culture; and (iii) can efficiently secrete recombinant proteins. The advantages of a host cell that does not secrete chitinase includes: (i) elimination of competition for chitin-binding sites between CBD-tagged proteins and endogenous chitinase; (ii) elimination of the risk of contamination of chitin-immobilized fusion proteins by endogenous chitinase; and (iii) elimination of degradation of the target chitin matrix by endogenous chitinase.

Suitable host cells include production lines of various insect cell cultures and mammalian cell lines as well as yeast production strains and bacterial cells.

Examples of cells from which proteins are secreted for purposes of manufacture include *E. coli*, *Salmonella* species, *Bacillus* species, *Streptomyces* species, etc.), plant cells (e.g. *Arabidopsis* species, *Taxus* species, *Catharanthus* species, *Nicotiana* species, *Oryza* species, soybeans, alfalfa, tomatoes, etc.), fungal cells (e.g. *Kluyveromyces* species, *Saccharomyces* species, *Pichia* species, *Hansenula* species, *Yarrowia* species, *Neurospora* species, *Aspergillus* species, *Penicillium* species, *Candida* species, *Schizosaccharomyces* species, *Cryptococcus* species, *Coprinus* species, *Ustilago* species, *Magnaporth* species, *Trichoderma* species, etc.), insect cells (e.g. Sf9 cells, Sf12 cells, *Trichoplusia ni* cells, *Drosophila* species etc.), or mammalian cells (e.g. primary cell lines, HeLa cells, NSO cells, BHK cells, HEK-293 cells, PER-C6 cells, etc). These cells may be grown in cultures ranging from microliter volumes to multiliter volumes.

A *Kluyveromyces* species is used here to illustrate how secreted proteins fused to CBD can be rapidly and easily separated from mixtures. The yeasts of the genus *Kluyveromyces* according to embodiments of the invention include the yeasts as defined by van der Walt in *The Yeasts*, ed. N. J. W. Kregervan Rij: Elsevier, New York, N.Y., p. 224 (1987) and include *K. marxianus* var. *lactis* (*K. lactis*), *K. marxianus* var. *marxianus* (*K. fragilis*), *K. marxianus* var. *drosophilarum* (*K. drosophilarum*) and *K. waltii* and other strains classified as *Kluyveromyces* in the art.

In those host cells that naturally secrete one or more chitinases, a chitinase deletion mutant can be made by a genetic modification. Genetic modification refers to any of suppression, substitution, deletion or addition of one or more bases in the target gene. Such modifications can be obtained in vitro (on isolated DNA) or in situ, for example, by means of genetic engineering techniques, or alternatively by exposing the host cells to mutagenic agents, such as radiation (X ray, gamma ray, ultra violet rays and the like), or chemical agents capable of reacting with various functional groups of the bases of DNA, and for example alkylating agents: ethyl methane-sulphonate (EMS), N-methyl-N'-nitro-N-nitrosoguanidine, N-nitroquinoline 1-oxide (NQO), bialkylating agents, intercalating agents and the like. Furthermore, the expression of the target gene may be suppressed by modifying part of the region encoding the chitinases and/or all or part of the transcriptional promoter region.

The genetic modifications can also be obtained by gene disruption. An example of gene disruption of chitinase is provided in Example 1 for *Kluyveromyces lactis*. The method described in the example is broadly applicable to any *Kluyveromyces* species.

In Example 1, a chitinase gene encoding KlCts1p was disrupted in an industrial *K. lactis* strain (GG799) that preferably lacks the *K. lactis* killer plasmid. The disruption occurred by substituting a portion of the chitinase gene, for example, the first 168 amino acids of the naturally occurring *K. lactis* chitinase gene with a selectable marker gene such as G418 resistance cassette.

*K. lactis* GG799 Δcts1 cells were capable of achieving the same high cell density as wild-type cells in culture (Example 2), producing no proteins with detectable chitin binding or chitinolytic activities (FIG. 3A), and could abundantly secrete recombinant protein (FIG. 6). This strain proved well suited as a host for production of recombinant CBD-tagged protein.

For production purposes, it is desirable that a chitinase-negative mutant host cell will achieve a similar high cell density as wild-type cells in culture despite the lack of secreted proteins with detectable chitin binding or chitinolytic activities and these cells can abundantly secrete recombinant protein. The chitinase-negative host cells may thus be used in fermentation to efficiently make purified recombinant proteins linked to CBD either directly or via a linker peptide or linking chemical groups that have industrial utility.

Design and Use of Vectors for Expressing and Secreting High Levels of Protein in Yeast Examples of expression vectors for various yeasts are described in Muller et al. Yeast 14:1267-1283 (1998) and also in U.S. Pat. No. 4,859,596, U.S. Pat. No. 5,217,891, U.S. Pat. No. 5,876,988, U.S. Pat. No. 6,051,431, U.S. Pat. No. 6,265,186, U.S. Pat. No. 6,548,285, U.S. Pat. No. 5,679,544 and U.S. application Ser. No. 11/102,475 for *Kluyveromyces*.

Expression vectors may be exogenous. For example, YEp24 is an episomal shuttle vector used for gene overexpression in *Saccharomyces cerevisiae* (New England Biolabs, Inc., Ipswich, Mass.). Other examples of episomal shuttle vectors for this organism are pRS413, pRS414, pRS415 and pRS416. Autonomously replicating vectors in *Kluyveromyces* include pKD1 (Falcone et al., Plasmids 15:248 (1986); Chen et al., *Nucl. Acids Res.* 14:4471 (1986)), pEW1 (Chen et al., *J. General Microbiol.* 138:337 (1992)) In addition to full pKD1 vectors, smaller vectors containing the pKD1 origin and a cis-acting stability locus (CSL) have been constructed and used for heterologous protein expression in *K. lactis* (Hsieh, et al. *Appl. Microbiol. Biotechnol.* 4:411-416 (1998)). Other episomal vectors also replicate in *K. lactis*. A plasmid carrying both a centromere (cen) and autonomously replicating sequence (ars) has been used for expression cloning of fungal cDNAs in *K. lactis* (van der Vlug-Bergmans, et al. *Biotechnology Techniques* 13:87-92 (1999)). Additionally, vectors containing a *K. lactis* ARS sequence (KARS) have been used to express fungal α-galactosidase (Bergkamp, et al. *Curr Genet.* 21:365-70 (1992)) and a plant α-amylase (Strasser et al. *Eur. J. Biochem.* 184:699-706 (1989)).

Other vectors may be integrated into the host genome. For example, U.S. Pat. No. 6,602,682, U.S. Pat. No. 6,265,186 and U.S. application Ser. No. 11/102,475 for plasmids that are integrated into the genome of *Klyveromyces*.

The vector should contain at least one or more of the following: (i) a strong yeast promoter; (ii) DNA encoding a secretion leader sequence (if secretion of the protein into the medium is desired); (iii) the gene encoding the protein to be expressed; (iv) a transcription terminator sequence; and (v) a yeast-selectable marker gene. These sequence components are typically assembled in a plasmid vector in *E. coli* then transferred to yeast cells to achieve protein production. Vectors of this type are referred to as shuttle vectors.

Whereas shuttle vectors are preferable because they can be prepared in *E. coli* prior to transforming the host cell, the present embodiments are not limited to shuttle vectors.

For example, DNA fragments capable of integrating into the yeast genome could be constructed by PCR or Helicase-Dependent Amplication (HDA) and directly introduced into yeast cells. Alternatively, expression vectors could be assembled by cloning steps in bacteria other than *E. coli* or directly in yeast cells.

Overexpression of proteins in Kluyveromyces and more generally in yeast involves construction of a shuttle vector containing a DNA fragment with sequences suitable for directing high-level transcription of a gene of interest upon introduction into the yeast host. For example, $P_{LAC4}$ can function as a strong promoter for protein expression in yeast when present on an integrative plasmid or an episomal plasmid such as pKD1-based vectors, 2 micron-containing vectors, and centromeric vectors. The secretion leader sequence (if secretion of the protein into the medium is desired) may include a *S. cerevisiae* α-MF pre-pro secretion leader peptide. Other prokaryotic or eukaryotic secretion signal peptides (e.g. *Kluyveromyces* α-mating factor pre-pro secretion signal peptide, *Kluyveromyces* killer toxin signal peptide) or synthetic secretion signal peptides can also be used. Alternatively, a secretion leader can be omitted from the vector altogether to achieve cellular expression of the desired protein.

A shuttle vector allows for the propagation of cloned genes in bacteria prior to their introduction into yeast cells for expression. However, yeast expression systems that utilize wild-type $P_{LAC4}$ can be adversely affected by the serendipitous expression of protein from genes under control of $P_{LAC4}$ in bacterial host cells such as *E. coli*. This promoter activity can interfere with the cloning efficiency of genes whose translational products are deleterious to bacteria.

$P_{LAC4}$ variants with mutated Pribnow box-like sequences can be created by site-directed mutagenesis that substantially retain their ability to function as strong promoters in *Kluyveromyces* species exemplified but not limited to *K. lactis*. These mutant promoters function substantially as well or better than the unmutated Pribnow box-like sequences in wild-type $P_{LAC4}$.

The term "mutation" is here intended to include any of: a substitution, a deletion or an addition of one or more nucleotides in a wild-type DNA sequence.

In an embodiment of the invention, the fungal expression host is the yeast *Kluyveromyces* species and the bacterial host is *E. coli* and a series of $P_{LAC4}$ variants characterized as follows: (a) the −198 to −212 region of the promoter for example at positions −201, −203, −204, −207, −209 and −210 do not substantially interfere with the ability of the promoter to function as a strong promoter in *K. lactis*; (b) the −133 to −146 region of the promoter for example at positions −139, −140, −141, −142 and −144 do not substantially interfere with strong promoter activity; or (c) the −198 to −212 and −133 to −146 regions can be incorporated; (d) a hybrid promoter was created that consists of 283 bp (−1 to −283) of the *S. cerevisiae* (Sc) PGK promoter replacing the −1 to −283 region of *K. lactis* $P_{LAC4}$. These substitutions are described in detail in U.S. application Ser. No. 11/102,475.

An example of a transcription terminator sequence is $TT_{LAC4}$.

The yeast-selectable marker gene can be for example a gene that confers resistance to an antibiotic (e.g. G418, hygromycin B, and the like), a gene that complements a strain auxotrophy (e.g. ura3, trp1, his3, lys2 and the like) or an acetamidase (amdS) gene. Expression of acetamidase in transformed yeast cells allows for their growth on medium lacking a simple nitrogen source but containing acetamide. Acetamidase breaks down acetamide to ammonia, which can be utilized by cells as a source of nitrogen. A benefit of this selection method is that it enriches transformant populations for cells that have incorporated multiple tandem integrations of a pKLAC1-based expression vector and that produce more recombinant protein than single integrations (FIG. 5).

The above-described vectors containing mutants of $P_{LAC4}$ have been inserted into an E. coli/Kluyveromyces integrative shuttle vector, for example, pGBN1 and pKLAC1 (U.S. application Ser. No. 11/102,475), respectively, which integrates into the Kluyveromyces genome after transformation of competent host cells and subsequently directs protein expression.

U.S. application Ser. No. 11/102,475 describes shuttle vectors containing a mutant $P_{LAC4}$ for use in yeast and more particularly Kluyveromyces exemplified by K. lactis providing an improvement over vectors described in U.S. Pat. No. 4,859,596, U.S. Pat. No. 5,217,891, U.S. Pat. No. 5,876,988, U.S. Pat. No. 6,051,431, U.S. Pat. No. 6,265,186, U.S. Pat. No. 6,548,285, U.S. Pat. No. 5,679,544. This improvement results from the utility for expression in yeast of modified LAC4 and its inability to express proteins in E. coli thus avoiding problems resulting from toxicity in bacterial cloning host cells.

Introduction of DNA Vectors into Host Cells

Methods of introducing DNA into host cells are well established for eukaryotic and prokaryotic cells (Miller, J. F. Methods Enzymol. 235:375-385 (1994); Hanahan, D. et al., Methods Enzymol. 204:63-113 (1991)). In yeast, standard methods for introducing DNA into cells include genetic crosses, protoplast fusion, lithium-based transformation, electroporation, conjugation, or any other technique described in the literature for example, Wang et al. Crit. Rev Biotechnol. 21(3):177-218 (2001), Schenborn et al. Methods Mol. Biol. 130:155-164 (2000), Schenborn et al. Methods Mol. Biol. 130:147-153 (2000). As regards transformation of the Kluyveromyces yeasts, established techniques are described in Ito et al. (J. Bacteriol. 153:163 (1983)), Durrens et al. (Curr. Genet. 18:7 (1990)), Karube et al. (FEBS Letters 182:90 (1985)), and Patent Application EP 361 991.

Properties of CBDs Including Elution Properties

CBD as a component of chitinase can be obtained from many different sources, for example, fungi, bacteria, plants and insects. Any CBD originating from a chitinase may be used herein although CBDs separated from chitinase catalytic activity are preferred. Also preferred is a CBD that is capable of disassociating from chitin under non-denaturing conditions different from the conditions that permit binding. Not all CBDs are capable of disassociating from chitin under non-denaturing conditions. For example, B. circulans CBD binds tightly to chitin and is not reversible unless a mutation is introduced into the protein as described in U.S. Pat. No. 6,897,285, U.S. Publication Nos. 2005-0196804 and 2005-0196841. In contrast, Kluyveromyces species produce a CBD that binds tightly to chitin but can be reversibly disassociated under altered conditions such as NaOH (see Examples 5 and 6).

Kluyveromyces produce abundantly expressed secreted endo-chitinase (KCBD), which is shown here by way of an example to be an effective affinity tag to allow for the reversible immobilization or purification of alkaliphilic or alkali-tolerant proteins. The KCBD can bind chitin in the absence of the catalytic domain (see for example FIG. 4D), function as an affinity tag on a heterologously expressed protein in Kluyveromyces as exemplified in FIGS. 4D and 6B, and dissociate from chitin in NaOH within a range of about 5 mM to 500 mM, whereas the CBD from B. circulans (BcCBD) cannot.

Characteristics of Chitin for Binding the CBD

Synthetic or naturally occurring chitin may be used for binding CBD fusion proteins. An example of synthetic chitin is acetylated chitosan, polymerized N-acetylglucosamine monosaccharides, polysaccharides or oligosaccharides, or polymerized glucosamine monosaccharides, oligosaccharides or polysaccharides where the glucosamine is subsequently chemically acetylated.

Examples of naturally occurring chitin are chitin derived from crab shells, insect exoskeletons, or fungal cell walls or from any source known in the art.

The chitin may be optionally immobilized on a substrate as described in FIG. 7. An example of a substrate is a polymer such as a plastic. Alternatively, chitin may be aggregated to form for example: suspensions, colloids, beads, columns, matrices, sheets, or membranes. The chitin may be sterilized for addition to the fermentation media during fermentation or may be used in an unsterilized form for binding fusion protein at the end of the fermentation process.

Generally Applicable Approach for Concentrating any Secreted Protein Fused to a CBD Using Chitin-Coated Magnetic Beads The chitin substrate for binding secreted CBD fusion protein may optionally be magnetized for ease in removing the target protein from culture media. Magnetized chitin is made by combining chitin with magnetic material. The magnetic material may be dispersed fragments such as iron filings. In a preferred embodiment the magnetized chitin is in the form of beads although the magnetized chitin may be used as a coating to an additional material that may optionally be inert. Whereas in a preferred embodiment, the magnetized material is magnetized chitin, other magnetic materials may be used that have the properties of (a) being capable of binding a target protein or expressed as a fusion with the target protein; and (b) being capable of binding to a material that can be magnetized.

In one embodiment, magnetized chitin beads (New England Biolabs, Inc., Ipswich, Mass.) are used to bind secreted CBD fusion protein. The size of the beads is not critical although beads formed from a size less than 200 nm in diameter have an advantage in that they pass through a sterilizing filter and form a colloid in media until a magnetic force is applied (see for example, 5,160,726). Larger beads may also be used. The chitin beads may be solid (for example New England Biolabs, Inc., Ipswich, Mass.) or porous (for example, JP 62151430). Moreover, the beads may be magnetized by a variety of means for example, by dispersing iron filings throughout the beads or by forming beads with an iron core (by coating the iron with chitin) (see for example 5,262, 176). Although the magnetized chitin used here is in the form of beads in a preferred embodiment, other shapes and sizes of chitin surfaces are not intended to be precluded.

Magnetic chitin beads can also be added to growth medium during or after growth of a cell culture, or after clearing grown cells from a culture (FIG. 9B). Accordingly, it has been shown here that magnetized chitin beads can be sterilized without significantly altering their binding properties. When chitin beads are added to cultivation medium during cell growth, it is preferable that the beads be sterilized.

Typically, maximum binding of CBD-tagged proteins to chitin beads (FIG. 9B, Steps 4a and 4b) will occur within 1 hour at 4° C., however, other temperatures and timeframes are also possible. Proteins immobilized to magnetic chitin beads are harvested in a magnetic field (FIG. 9B, Steps 5a and 5b) and cells, contaminating proteins and growth medium are washed away from the beads (FIG. 9B, Step 6). Chitin bead-protein complexes are then released from the magnetic field (FIG. 1B, Step 7) and harvested proteins can remain immobilized on the chitin magnetic beads indefinitely (FIG. 9B, Step 8b) or can be dissociated from chitin (FIG. 9B, Step 8a) if an elutable CBD was used as the affinity tag.

By adding magnetized chitin beads to medium in the fermentation vessel, a very efficient one step process for recovering a target protein can thus be achieved. The cells grow in the medium containing the magnetized chitin beads so that the secreted CBD-tagged protein binds to the beads during culturing, and can be harvested directly from the media by the simple step of applying a magnetic force from a magnet external to the fermentation vessel or as desired, internal to the fermentation vessel (see FIGS. 9-11). This approach requires that the magnetized chitin beads be sterilized. The yield from sterilized chitin beads of a size of 50-70 μm added at the beginning or during fermentation has been shown here to be similar to the yield of protein obtained when beads are added at the completion of fermentation (FIG. 8).

A compelling feature of the present approach for concentrating secreted protein from a large volume is its universality. The methodology takes advantage of the ability of a chitin-binding domain to bind to chitin when fused to an additional protein where the function of the additional protein is not compromised by the presence of the CBD.

By ensuring that the cells secreting the fusion protein do not natively produce proteins that bind chitin, competitive binding and contamination is avoided. CBD binds chitin with significant avidity. Causing the desired protein CBD fusion protein to be recovered from the chitin bead can be achieved either by mutating the CBD so that binding can be reversed under controlled conditions to release the fusion protein (U.S. Pat. No. 6,897,286) or alternatively by using an intein cleavage system or protease cleavage to release the protein from the CBD-chitin complex (WO 2004/053460, U.S. Pat. No. 5,643,758). Additionally, the CBD tag can be liberated from the desired protein by digestion with a protease (e.g. enterokinase, genenase, furin, factor X, etc.) if a proteolytic cleavage site is present between the CBD and the desired protein.

The robust nature of the CBD-chitin interaction allows CBD-tagged proteins to rapidly become immobilized to magnetized chitin in whatever form for example beads.

Where the magnetized chitin is in the form of beads, the chitin beads containing the bound CBD-tagged protein can be harvested in a magnetic field within seconds. If desired, the CBD-tagged protein can be dissociated from the magnetized substrate by incubation in an elution buffer (if an elutable CBD was used). Advantages of this method include improved speed, cost effectiveness and simplicity.

Magnetic separation devices that fit common laboratory tubes (e.g. 96-well microtiter dishes, microcentrifuge tubes, 15 ml Falcon tubes, 50 ml Falcon tubes, 250 ml Nalgene bottles, etc.) are used for harvesting CBD-tagged proteins from a few microliters to several liters of culture medium (FIGS. 3-6). The procedures are easily scalable to allow for harvesting CBD-tagged proteins from larger volumes of medium. In preferred embodiments, magnets are constructed from rare earth metals (e.g. neodymium, samarium cobalt, etc.), but other types of magnets can also be used (e.g. ferrites, ceramics, electromagnets, etc).

Use of the Expression System

Production and separation of a target protein from a mixture is required for proteins used as pharmaceuticals, in food or for industry. The list of proteins for which fermentation-based production presently exists or is desirable is very large. A few examples include superoxide dismutase, catalase, amylases, lipases, amidases, glycosidases, xylanases, laccases, ligninases chymosin and the like, or any fragment or derivative thereof, blood derivatives (such as serum albumin, alpha- or beta-globin, coagulation factors, and for example factor VIII, factor IX, von Willebrand's factor, fibronectin, alpha-1 antitrypsin, and the like, or any fragment or derivative thereof), insulin and its variants, lymphokines such as interleukins, interferons, colony-stimulating factors (G-CSF, GM-CSF, M-CSF and the like), TNF and the like, or any fragment or derivative thereof, growth factors (such as growth hormone, erythropoietin, FGF, EGF, PDGF, TGF, and the like, or any fragment or derivative thereof), apolipoproteins and their molecular variants, antigenic polypeptides for the production of vaccines (hepatitis, cytomegalovirus, Epstein-Barr virus, herpes virus and the like), single chain antibodies (ScFv) or alternatively polypeptide fusions such as especially fusions containing a biologically active part fused to a stabilizing part.

All references cited herein are incorporated by reference.

EXAMPLES

Example 1

Materials and Methods for Subsequent Examples

Yeast Strains, Culturing Conditions and Conditions for Transformation

Strains of *K. lactis* and *S. cerevisiae* (Table 1) were routinely cultured in YPD medium (1% yeast extract, 2% peptone, and 2% glucose) or YPGal medium (1% yeast extract, 2% peptone, and 2% galactose) at 30° C.

TABLE 1

Yeast strains used in this study.

| Organism | Strain | Genotype | Source |
|---|---|---|---|
| *K. lactis* | GG799 | MATα [pGKI1° pGKI2°] | This study |
|  | PCKI1 | MATα cts1::Kan$^R$ [pGKI1° pGKI2°] | This study |
|  | PCKI2 | MATα LAC4::BcCBD-HSA [pGKI1° pGKI2°] | This study |
|  | PCKI3 | MATα LAC4::KlCBD-HSA [pGKI1° pGKI2°] | This study |
|  | CBS 2359 | MATa [pGKI1$^+$ pGKI2$^+$] | ATCC 8565 |
|  | CBS 683 | MATα [pGKI1$^+$ pGKI2$^+$] | ATCC 56498 |
|  | PRY297 | MATα ade1 ade2 [pGKI1$^+$ pGKI2$^+$] | ATCC 46794 |
|  | PRY298 | MATα ade1 ade2 [pGKI1$^+$ pGKI2$^+$] | ATCC 52735 |
|  | PRY299 | MATa uraA [pGKI1$^+$ pGKI2$^+$] |  |

TABLE 1-continued

Yeast strains used in this study.

| Organism | Strain | Genotype | Source |
|---|---|---|---|
| S. cerevisiae | BY4741 | MATa his3Δ1 leu2Δ0 met15Δ0 ura3Δ0 | Research Genetics* |
| | 6947 | MATa his3Δ1 leu2 Δ0 met15 Δ0 ura3 Δ0 cts1:: kanMX4 | Research Genetics* |
| | PCSc1 | MATa his3Δ1 leu2Δ0 met15Δ0 ura3Δ0 cts1:: kanMX4 [pKlCTS1] | This study |

*Research Genetics, Invitrogen, Carlsbad, CA

Transformation of *K. lactis* and *S. cerevisiae* was achieved using electroporation. Transformants of *K. lactis* were selected by growth on YPD agar containing 200 mg G418 ml$^{-1}$ whereas *S. cerevisiae* transformants were obtained by growth on SD medium (0.67% yeast nitrogen base, 2% glucose) or SGal medium (0.67% yeast nitrogen base, 2% galactose) containing the appropriate supplements needed to complement strain auxotrophies.

Detection and Isolation of Secreted *K. lactis* Chitin-Binding Proteins

Western blotting was used to detect secreted *K. lactis* proteins that cross-reacted to a polyclonal anti-chitin-binding domain antibody (α-CBD) raised against the chitin-binding domain derived from *Bacillus circulans* chitinase A1 (New England Biolabs, Inc., Ipswich, Mass.).

(a) Spent culture medium was isolated from *K. lactis* GG799 cultures following 48-96 hours growth by centrifugation at 4000× g for 10 minutes.

After centrifugation, proteins in the spent medium were separated by SDS-PAGE on a 4-20% Tris-Glycine polyacrylamide gel (Daiichi Pharmaceutical Corp., Montvale, N.J.) and transferred to Protran nitrocellulose membrane (Schleicher & Schuell Bioscience, Keene, N.H.). The membrane was blocked overnight in phosphate-buffered saline containing 0.05% Tween 20 (PBS-T) and 5% non-fat milk (w/v) at 4° C. and probed with α-CBD polyclonal antibodies (1:2000 in PBS-T containing 5% non-fat milk) followed by a horseradish peroxidase conjugated anti-rabbit secondary antibody (Kirkegaard & Perry Laboratories, Gaithersburg, Md.); 1:2000 in PBS-T containing 5% non-fat milk). Protein-antibody complexes were visualized using LumiGlo™ detection reagents (Cell Signaling Technologies, Beverly, Mass.).

(b) To isolate secreted proteins that bind chitin, *K. lactis* GG799 cells were grown in 20 ml YPD medium for 96 hours. Cells were removed from the culture by centrifugation and the spent medium was transferred to a fresh tube containing 1 ml of water-washed chitin beads (New England Biolabs, Inc., Ipswich, Mass.) and incubated at room temperature with gentle rotation for 1 hour. The chitin beads were harvested by centrifugation and washed with 10 ml of water. Approximately a 50 µl volume of protein-bound chitin beads was removed and boiled in protein loading buffer for 2 minutes to elute bound proteins, after which the eluted proteins were separated by SDS-PAGE and subjected either to Western analysis with α-CBD polyclonal antibodies or to amino-terminal protein sequencing.

Analysis of Chitin-Binding Properties of *K. lactis* Chitinase Derived Chitin-Binding Domain (KlCts1p CBD)

KlCts1p from 20 ml of *K. lactis* GG799 spent culture medium was bound to a 1 ml volume of chitin beads as described above. The KlCts1p-bound beads were washed with 10 ml water and resuspended in 1.5 ml of water. Minicolumns were prepared by dispensing 100 µl aliquots of the KlCts1p-bound beads into individual disposable columns (Bio-Rad Laboratories, Hercules, Calif.). A 1 ml volume (~10 bed volumes) of the following buffers was passed over separate minicolumns: 50 mM NaCitrate pH 3.0, 50 mM NaCitrate pH 5.0, 100 mM Glycine-NaOH pH 10.0, un-buffered 20 mM NaOH pH 12.3, 5 M NaCl and 8 M Urea. Each column was then washed with 2 ml water, after which the beads were resuspended in 200 µl of water, transferred to microcentrifuge tubes and collected by brief centrifugation. Protein remaining bound to the chitin was eluted by boiling the beads in 50 ml of 3× SDS-PAGE loading buffer (New England Biolabs, Inc., Ipswich, Mass.) for 5 minutes. Eluted proteins were separated by SDS-PAGE and detected by Western analysis as described above.

A KlCts1p elution profile using varying concentrations of NaOH (0-40 mM) was carried out in a similar manner. Aliquots (100 µl) of chitin-bound KlCts1p were prepared as described above and were distributed into microfilter cups (Millipore, Billerica, Mass.) that had been inserted into 1.5 ml microcentrifuge tubes to create spin columns. The flow-through was collected by microcentrifugation at 15,800× g for 1 min and discarded. The beads were then resuspended in 100 µl of NaOH at each desired concentration (0-40 mM) and the eluates collected by centrifugation at 15,800× g for 1 min. Chitinase activity in each eluate was measured as described below.

Disruption of the *K. lactis* Chitinase Gene (KlCTS1)

A PCR-based method was used to construct a linear DNA disruption fragment consisting of an ADH2 promoter-G418 resistance gene cassette having 80-82 bp of KlCTS1 DNA on either end. When integrated at the KlCTS1 locus, this fragment causes replacement of DNA encoding the first 168 amino acids of KlCts1p with the G418-resistance cassette. Primers containing DNA that hybridizes to the ADH-G418 sequence (no underline) and having tails consisting of KlCTS1 DNA sequence (underlined), 5'-CCAGTAATGCAACTATCAATCATTGTGTTAAACTG-GTCACCAGAAATACAAGATATCAAAAATTACTAA-TACT-ACCATAAGCCATCATCATATCGAAG-3' (SEQ ID NO:1) and 5'-CCAAACTAG-CGTATCCGGTTGGATTATTGTTTTCGATATCGA-AATCGAAACCATCGACGACAGCAGTGTCGAATGGT-CTTTCCCCGGGGTGGGCGAAG AACTCC-3' (SEQ ID NO:2), were used to amplify the disrupting DNA fragment from the ADH2-G418-containing vector pGBN2 using Taq DNA polymerase. Amplified product was used to transform *K. lactis* GG799 cells and colonies were selected on YPD agar containing 200 mg G418 ml$^{-1}$. Whole-cell PCR using a KlCTS1-specific forward primer 5'-GGGCACAACAATG-GCAGG-3' (SEQ ID NO:3) (designed upstream of the integration site) and a G418-specific reverse primer 5'-GC-CTCTCCACCCAAGCGGC-3' (SEQ ID NO:4) was used to amplify an ~600 bp diagnostic DNA fragment from cells that had correctly integrated the disrupting DNA fragment at the KlCTS1 locus. Of 20 transformants tested in this manner, two Δcts1 *K. lactis* strains were identified and further characterized.

Heterologous Expression of KlCTS1 in *S. cerevisiae*

To express KlCTS1 in *S. cerevisiae*, the gene was PCR-amplified with primers 5'-GGC GGATCCGCCACCATGTTTCACCCTCGTTTACTT-3' (BamH I site underlined) (SEQ ID NO:5) and 5'-ACAT GCATGCCTAGAAGACGACGTCGGGTTTCAA-3' (Sph I site underlined) (SEQ ID NO:6) and cloned into the BamH I-Sph I sites of pMW20 (31) to place expression of KlCTS1 under the control of the galactose-inducible/glucose-repressible *S. cerevisiae* GAL10 promoter. This expression construct was introduced into *S. cerevisiae* Δcts1 strain RG6947 by transformation. To induce production of KlCtsp1, 2 ml starter cultures were grown in SD medium containing 20 mg uracil ml$^{-1}$ overnight at 30° C., after which, 1 ml of each culture was used to inoculate 20 ml YPD and 20 ml YPGal cultures. Each culture was grown overnight with shaking at 30° C. prior to analysis of the spent culture medium for chitinase production and cell morphology by microscopy.

Chitinase Activity Measurements

Chitin oligosaccharides of 1-4 GlcNAc residues and each derivatized with 4-methyl umbelliferone (4-MU) were used as substrates: 4-methylumbelliferyl N-acetyl-β-D-chitotrioside (4MU-GlcNAc), 4-methylumbelliferyl N,N'-diacetyl-β-D-chitotetraoside (4MU-GlcNAc$_2$), 4-methylumbelliferyl N,N',N"-triacetyl-β-D-chitotrioside (4MU-GlcNAc$_3$) or with 4-methylumbelliferyl N,N',N",N"'-tetraacetyl-β-D-chitotetraoside (4MU-GlcNAc$_4$) (Sigma-Aldrich Corp., St. Louis, Mo. and EMD Biosciences, San Diego, Calif.). Chitinase activity was determined by measuring the release of 4-MU using a Genios fluorescent microtiter plate reader (Tecan, San Jose, Calif.) and 340 nm/465 nm excitation/emission filters at 37° C. Reaction mixes in each well of 96-well black microtiter plates were 100 ml and contained 50 mM substrate, 1× McIlvaine's buffer (pH ranged from 4-7 in different experiments) and 5-10 ml of sample. Initial rates of release were recorded and enzyme units calculated as pmol of 4-MU release min$^{-1}$. Standard curves of 4-MU (Sigma-Aldrich Corp., St. Louis, Mo.) were prepared under conditions used for the reactions for conversion from fluorescent units.

Microscopy

Approximately 1-2 OD$_{600}$ units of cells were harvested and fixed in 1 ml of 2.5% (v/v) glutaraldehyde on ice for 1 hour. Cells were washed twice with water and resuspended in approximately 100 ml mounting medium (20 mM Tris-HCl pH 8.0, 0.5% N-propylgallate, 80% glycerol). In septum staining experiments, Calcofluor white (Sigma-Aldrich Corp., St. Louis, Mo.) was added to the mounting medium to a final concentration of 100 mg ml$^{-1}$. Cells were viewed with a Zeiss Axiovert 200M microscope using light phase Normaski imaging or fluorescent DAPI filter settings.

Cellular Chitin Measurements

Cells were extracted with KOH and the chitin in the alkali insoluble material was hydrolyzed to GlcNAc by chitinase for quantifying by a micro Morgan-Elson assay as previously described (Bulik, D. A., et al. *Eukaryot. Cell* 2:886-900 (2003)).

Example 2

Identification and Biochemical Characterization of *K. lactis* Chitinase (KlCts1p)

Figure 1:
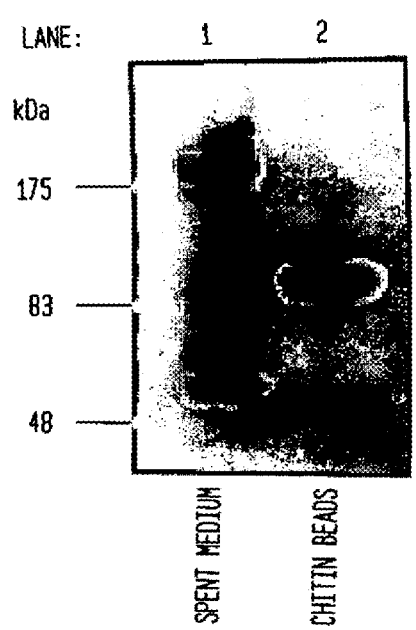

A polyclonal antibody raised against *B. circulans* ChiA chitin-binding domain (α-CBD) was used in Western blotting analysis of *K. lactis* GG799 spent culture medium to identify native secreted *K. lactis* proteins that contain a cross-reacting chitin-binding domain (FIG. 1).

Secreted proteins in 10 ml of unconcentrated *K. lactis* GG799 spent culture medium (96 hour growth) were separated on a 4-20% polyacrylamide Tris-glycine SDS gel and screened for the presence of a chitin-binding domain by Western blotting with a polyclonal antibody raised to the *B. circulans* chitinase A1 chitin-binding domain (lane 1). Secreted proteins were bound to chitin beads and eluted directly into SDS-PAGE loading buffer by boiling for 2 minutes prior to separation by SDS-PAGE (lane 2).

To test if any of these proteins were able to bind chitin, spent culture medium was mixed with chitin beads and rotated for 1 hour at room temperature. The chitin beads were washed with water and bound proteins were eluted directly into SDS-PAGE loading buffer by boiling. Western blotting indicated that only the 85 kDa a-CBD cross-reacting protein was able to bind chitin (FIG. 1, lane 2). Protein purified directly from chitin beads in this manner was subjected to N-terminal protein sequencing resulting in the identification of the first 20 amino-terminal amino acids of the mature protein (FDINAKDNVAVYWGQASAAT) (SEQ ID NO:7). A tBLASTn search using this amino acid sequence as a query to probe sequence databases identified a partially sequenced *K. lactis* gene having a translation that exactly matched the query sequence and that had significant homology to the *S. cerevisiae* extracellular chitinase Cts1p (ScCts1p).

Cloning KlCTS1 and Sequence Analysis

At the onset of this work, the sequence of the *K. lactis* genome had not yet been reported. Therefore, a combination of Southern hybridization and anchored PCR was used to clone the remainder of a partial KlCTS1 sequence originally identified by database searching with the tBLASTn algorithm (see above). The KlCts1p sequence was identical to the translated product of *K. lactis* ORF KLLA0C04730g in the recently reported *K. lactis* genome sequence (Dujon B., et al. *Nature* 430:35-44 (2004)).

KlCTS1 encodes a protein with 551 amino acids having a molecular weight of 85 kDa as determined by SDS-PAGE. KlCTS1p is 53% identical and 82% similar to the *S. cerevisiae* Cts1p chitinase, and has a similar modular domain organization consisting of a signal peptide, a catalytic domain, a Ser/Thr rich domain and a chitin-binding domain (FIG. 2A). Signal P software (Nielson et al. *Protein Eng.* 10:1-6 (1997)) predicted the presence of a signal peptide that is cleaved after A$^{19}$ (FIG. 2A). This is in agreement with the amino-terminal protein sequence determined from purified secreted KlCts1p that begins at F$^{20}$. Amino acid homology between the predicted KlCts1p catalytic domain and those of other chitinases indicates that KlCts1p belongs to chitinase family 18 (FIG. 2B). Additionally, SMART domain prediction software (Letunic, I., et al. *Nucl. Acids Res.* 30:242-244 (2002) and Schultz, J., et al. *PNAS* 95:5857-5864 (1998)) indicates the presence of a C-terminal type 2 chitin-binding domain containing six conserved cysteine residues (FIG. 2C).

The catalytic properties of both KlCts1p and *S. cerevisiae* chitinase (ScCts1p) were compared. Because *S. cerevisiae* Cts1p has an acidic pH optimum (Kuranda, M., et al. *J. Biol. Chem.* 266:19758-19767 (1991)), pH 4.5 was initially chosen for defining the substrate preferences of KlCts1p. As shown in FIG. 3B, chitinases from both yeasts hydrolyze both 4MU-GlcNAc$_3$ and 4MU-GlcNAc$_4$ substrates. However, the *K. lactis* chitinase differs from ScCts1p in the extent to which is prefers 4MU-GlcNAc$_4$ to 4MU-GlcNAc$_3$. Similar results to those shown for *K. lactis* strain GG799 were observed for chitinase secreted from strains CBS2359 and CBS683. Additionally, KlCts1p showed maximum activity at pH 4.5, approximately 0.5 pH units more alkaline than that of ScCts1p (FIG. 3C).

KlCts1p CBD-Chitin Affinity Analysis

The association of KlCts1p and chitin beads was examined under a range of conditions. FIG. 4A shows that chitin association of KlCts1p is stable in 5M NaCl and in buffers at pH 3, pH 5 and pH 10. In 8 M urea, a condition that normally denatures proteins, only about 60% of chitin-bound KlCts1p dissociated from the chitin beads. However, complete dissociation was observed in 20 mM NaOH at pH 12.3. An elution profile of chitin-bound KlCts1p revealed that an equal amount of the protein eluted in the first two fractions (including the void volume) suggesting that destabilization of KlCts1p-chitin association occurs immediately in 20 mM NaOH (FIG. 4B). Surprisingly, KlCts1p eluted in this manner retained chitinolytic activity (FIG. 4C). In fact, measurement of chitinase activity pre-chitin binding and post-elution with 20 mM NaOH showed that nearly 100% of the chitinase activity was recovered.

To determine if the KlCts1p CBD can function: i) independently of the KlCts1p catalytic domain; and ii) as an affinity tag on heterologously expressed proteins, human serum albumin (HSA) containing a C-terminal fusion to the CBD derived from amino acids 470-551 of KlCts1p (KlCBD) was secreted from K. lactis. For comparison, HSA was also fused to the B. circulans chitinase A1 type 3 CBD (BcCBD) and secreted from K. lactis in the same manner. CBD-fusion proteins were bound to chitin beads as described in Example 1 and their chitin affinities in the presence of 20 mM NaOH was determined. FIG. 4D shows that the HSA-KlCBD fusion protein fully dissociated from chitin beads in 20 mM NaOH, whereas the HSA-BcCBD fusion protein remained bound to chitin even after extensive washing with 20 mM NaOH. These results indicate that the KlCBD functions independently of the KlCts1p catalytic domain and that its dissociation from chitin in 20 mM NaOH is an intrinsic property. Furthermore, these data raise the possibility that the KlCBD could be used as an elutable affinity tag for the purification or reversible chitin-immobilization of alkaliphilic or alkali-tolerant proteins.

Disruption of KlCTS1

To examine the in vivo function of KlCts1p in K. lactis, the KlCTS1 allele was disrupted in haploid cells. A PCR-based method was used to assemble a DNA disruption fragment containing a kanamycin selectable marker cassette as described in Materials and Methods. This fragment was used to transform K. lactis cells to G418-resistance. Transformants were screened by whole-cell PCR for those that had integrated the disrupting DNA fragment at the KlCTS1 locus. Of 20 colonies tested, two had correctly integrated the disrupting DNA fragment (data not shown) indicating that KlCTS1 is not essential for viability of K. lactis. Additionally, K. lactis Δcts1 cells do not secrete chitinase as demonstrated by the absence of KlCts1p (FIG. 5A) and chitinolytic activity (FIG. 3A) in spent culture medium.

The growth and cell morphology of K. lactis wild-type (GG799) and Δcts1 cells was examined. In YPD medium, the Δcts1 strain grew as small clusters of loosely clumped cells that were easily dispersed into single cells upon brief sonication. Fluorescence microscopy of cells stained with the chitin-binding dye Calcofluor white, showed that Δcts1 cells are joined via their septa (FIG. 5B, right panel) suggesting these cells are unable to degrade septum chitin during cytokinesis. A similar phenotype has been observed for S. cerevisiae Δcts1 cells (Kuranda, M., et al. J. Biol. Chem. 266:19758-19767 (1991)). Therefore, the ability of KlCTS1 to restore normal cell separation to S. cerevisiae Δcts1 cells was tested. KlCTS1 was placed under the control of the GAL10 galactose-inducible promoter in a S. cerevisiae expression vector. S. cerevisiae Δcts1 cells expressing KlCTS1 secrete KlCts1p in galactose-containing medium (FIG. 6A) and do not form cell aggregates (FIG. 6B). Considered together, these data suggest that KlCTS1 and ScCTS1 encode functionally equivalent proteins that participate in cell separation, presumably by facilitating the degradation of septum chitin.

Characterization of K. lactis Chitinase-Deletion Mutants

The ability of Δcts1 cells to grow to high culture density was examined. The aggregation phenotype associated with K. lactis Δcts1 cells distorted measurements of cell density by light absorbance at 600 nm ($OD_{600}$) to less than 65% of wild-type cells. However, cultures of wild-type and Δcts1 cells grown for 48 hours produced nearly identical dry weight masses of cells. Additionally, total cellular chitin did not differ significantly between the two strains. Strain GG799 yielded 21.8±1.9 nmoles GlcNAc per milligram of dry cells and the Δcts1 strain yielded 20.8±1.0 nmoles GlcNAc per milligram of dry cells upon KOH extraction of cellular chitin and hydrolysis by chitinase. Therefore, despite their mild growth phenotype, Δcts1 cells remain capable of achieving the same cell densities in culture as wild-type cells suggesting that this strain background would be suitable for commercial production of CBD-tagged proteins.

Example 3

Preparation of pGBN2-HSA-KlCBD

To create a fusion between the CBD of KlCts1p and human serum albumin (HSA), primers 5'-GGA AGATCTGACTCCTGGGCTGTTACAAGA-3' (Bgl II site underlined) (SEQ ID NO:8) and 5'-ATAAGAAT GCGGCCGCCTAGAAGACGACGTCGGGTTTCAAATA-3' (Not I site underlined) (SEQ ID NO:9) were used to amplify a DNA fragment encoding the C-terminal 81 amino acids of KlCts1p with Deep Vent™ DNA polymerase (New England Biolabs, Inc., Ipswich, Mass.). The KlCts1p-CBD fragment was cloned into the Bgl II-Not I sites of the K. lactis integrative expression plasmid pGBN2 (New England Biolabs, Inc., Ipswich, Mass.) to produce pGBN2-KlCBD. HSA was amplified with primers 5'-CCGCTCGAGAAAA-GAGATGCACACAAGAGTGAGGTTGCT-3' (Xho I site underlined) (SEQ ID NO:10) and 5'-CGC GGATCCTAAGCCTAAGGCAGCTTGACTTGC-3' (BamH I site underlined) (SEQ ID NO:11) and cloned into the Xho I-Bgl II sites of pGBN2-KlCBD. When integrated in the K. lactis genome, the resulting expression construct produces a single polypeptide consisting of the S. cerevisiae a-mating factor pre-pro secretion leader (present in pGBN2), HSA, and KlCBD.

A control construct that produces HSA containing a carboxy-terminal type 3 CBD derived from the B. circulans chitinase A1 (BcCBD) was assembled in a similar manner. The primers 5'-GGAAGATCTACGACAAATCCTGGT-GTATCCGCT-3' (Bgl II site underlined) (SEQ ID NO:12) and 5'ATAAGAATGCGGCCGCTTATTGAAGCT-GCCACAAGGCAGGAAC-3' (Not I site underlined) (SEQ ID NO:13) were used to PCR-amplify the BcCBD from pTYB1 (New England Biolabs, Inc., Ipswich, Mass.). The amplified product was cloned into the Bgl II-Not I sites of pGBN2 to create pGBN2-BcCBD. HSA was amplified and cloned into the Xho I-Bgl II sites of pGBN2-BcCBD as described above.

Example 4

Production and Secretion of HSA-CBD in *K. lactis* Δcts1 Cells

The vector pGBN2-HSA-KlCBD (5 μg) was linearized with SacII and used to transform *K. lactis* Δcts1 cells via electroporation. Transformants were selected on yeast carbon base agar medium (Difco™, Becton Dickinson, Franklin Lakes, N.J.) containing 5 mM acetamide by growth at 30° C. for 4 days. An Individual transformant was used to start a 2 ml YPD (1% yeast extract, 2% peptone, 2% glucose) culture that was grown overnight at 30° C. A 1:100 dilution of the overnight culture was used to inoculate a 2 ml YPGal (1% yeast extract, 2% peptone, 2% galactose) culture. The culture was incubated at 30° C. for 48 hours with shaking. Spent culture medium was prepared by microcentrifugation of 1 ml of culture at 15,800×g for 2 min to remove cells. A 20 ml aliquot of cleared spent culture medium was transferred to a new tube, mixed with 10 ml of 3× Protein Loading Buffer and heated for 10 minutes at 95° C. A 20 ml aliquot was resolved on a 10-20% Tris-Glycine polyacrylamide gel and the secreted HSA-KlCBD fusion protein was detected by Coomassie staining.

Example 5

Purification of HSA-KlCBD Using Chitin Beads

To isolate secreted HSA-KlCBD by immobilization of the fusion protein to chitin, *K. lactis* Dcts1 cells harboring the integrated HSA-KlCBD expression fragment (see above) were grown in 20 ml YPD medium for 96 hours. Cells were removed from the culture by centrifugation and the spent medium was transferred to a fresh tube containing 1 ml of water-washed chitin beads (New England Biolabs, Inc., Ipswich, Mass.) and incubated at room temperature with gentle rotation for 1 hour. The chitin beads were harvested by centrifugation, washed with 10 ml of water and resuspended in 1 ml of water. Immobilized HSA-KlCBD was eluted by boiling an ~50 ml volume of protein-bound chitin beads in SDS Sample Buffer for 2 min, followed by microcentrifugation for 2 min to remove the chitin beads. Eluted HSA-Kl-CBD in the supernatant was visualized by SDS-PAGE and Coomassie staining or by Western analysis with a-CBD or a-HSA antibodies. Additionally, HSA-KlCBD can be eluted from the chitin beads by passage of 5 ml of 20 mM NaOH over the column. HSA produced in this manner is free from endogenous *K. lactis* proteins that fortuitously bind to or degrade chitin.

Example 6

Concentration of HSA-KlCBD Using Magnetized Chitin Beads

CBD-tagged human serum albumin (HSA-CBD) was used to demonstrate the association of a CBD-tagged protein with magnetic chitin beads during various stages of culture growth (see FIG. 8). Four 25 ml YPGal (1% yeast extract, 2% peptone, and 2% galactose) cultures of *K. lactis* strain GG799 Δcts1PCKl3 were innoculated with 100 ml of a 2 ml starter culture that had been grown for 24 hours at 30° C.

Culture 1: Prior to inoculation, 1 ml of settled chitin magnetic beads that had been sterilized by autoclaving for 20 min was added in the culture medium. The culture was then incubated for 72 hours at 30° C. with shaking at ~300 r.p.m.

Culture 2: At 24 hours of growth, 1 ml of sterile magnetic chitin beads was added to the culture medium. The culture was incubated for an additional 48 hours (72 hour total) at 30° C. with shaking at ~300 r.p.m.

Culture 3: After 72 hrs, 1 ml of chitin magnetic beads was added to the third culture followed by gentle shaking at room temperature for 1 hour.

Culture 4: The fourth culture was cleared of cells by centrifugation at 5000 r.p.m. for 5 min, after which 1 ml of magnetic chitin beads was added to the cleared spent culture medium followed by gentle shaking at room temperature for 1 hour.

Each culture was decanted into a standard 50 ml capped laboratory tube. Magnetic beads were harvested by inserting the tube into a 50 ml magnetic apparatus (FIG. 9) for 30 seconds followed by decanting the supernatant. The tube was then removed from the magnetic field and the pellet of magnetic chitin particles was washed with 40 ml of water and re-isolated in the magnetic field. This washing process was repeated a total of three times, after which the beads were transferred to four screw-capped microcentrifuge tubes. To elute the bound HSA-CBD, the beads in each tube were suspended in 250 ml of 3× protein loading buffer containing dithiothreitol (New England Biolabs, Inc., Ipswich, Mass.) and were heated for 5 minutes at 98° C. Eluted proteins in 5 ml of each sample were separated a 10-20% SDS-PAGE gel and visualized by Coomassie staining (FIG. 8). Eluted HSA-CBD was observed in each sample indicating that magnetic chitin beads successfully captured the CBD-tagged protein either during or after growth of the culture. The yield of captured HSA-CBD in each culture was estimated to be 4 mg L-1.

Example 7

Use of Magnetized Chitin Beads for Concentrating Secreted GluC-CBD Protein

To test the ability of the magnetized beads to concentrate CBD fusion protein from culture medium, 20 ml overnight cultures of *Bacillus circulans* transformed with DNA encoding a fusion protein (GluC-CBD, where GluC is an endoprotein from *Staphylococcus aureus*), were grown in 125 ml flasks. The DNA encoding the GluC was inserted into plasmid pGNB5, which contained the *B. circulans* CBD. Transformation of competent cells was achieved using standard techniques (Harwood and Cutting, *Molecular Biological Methods*, ed. John Wiley & Sons Ltd., New York, N.Y., pp. 33-35, 67, 1990). For comparative purposes, four cultures were grown: one containing the plasmid to express the GluC endoprotease, and three containing the plasmid for the fusion protein (GluC-CBD). For all experiments, a 5% bead volume was added to the culture. As a control, the culture containing the GluC construct was grown overnight in the presence of magnetic beads in order to examine nonspecific binding (FIG. 12, lane 2). Magnetic beads were added to the three GluC-CBD cultures at different times to see if incubation time effects binding capability. Culture 1 was grown overnight at 37° C. with shaking in the presence of the beads for the entire growth cycle (FIG. 12, lane 3). For Culture 2, the magnetic beads were added after 16 hours of growth at 37° C. and incubated for one hour at 37° C. with shaking (FIG. 12, lane 4). Culture 3 was grown overnight at 37° C. with shaking and the cells were removed by centrifugation (10,000 rpm for 10 minutes). The magnetic beads were added to the supernatant and incubated at room temperature for 1 hour with shaking (FIG. 12, lane 5). In all cases, the beads were harvested using a magnetic separation rack (New England Biolabs, Inc., Ipswich, Mass.), washed three times with 10 ml LB broth, and then twice with 10 ml of 1M NaCl. The beads were suspended in 1 ml of 1M NaCl, transferred to a 1.5 ml eppendorf tube, and centrifuged for 1 min at 10,000 rpm to remove liquid. The beads were suspended in 100 ml 3×SDS sample buffer with DTT and boiled for 5 minutes to remove protein. The beads were separated from the buffer by centrifugation at 10,000 rpm for 2 minutes. Samples were analyzed on a 10-20% Tricine gel, transferred onto PVDF membrane by Western Blot, and stained with Coomassie Blue. The identity of the eluted protein was confirmed by N-terminal sequencing. The results indicate that the secreted GluC-CBD fusion protein is the major protein bound by magnetic chitin beads, and can efficiently eluted by boiling in SDS sample buffer. The results also show that the beads can be added at any point during the experiment without altering their efficiency.

Example 8

Production of Luciferase and its Elution from Chitin Beads

The gene encoding the wild-type *K. lactis* CBD was cloned into the NotI/StuI restriction sites of vector pKLAC1 to create vector pKLAC1-KlCBD. The gene encoding *Gaussia* luciferase (GLuc) was then cloned into the XhoI/NotI restriction site of vector pKLAC1-KlCBD to create an N-terminal fusion with the vector derived secretion signal and a C-terminal fusion with the KlCBD gene. This construct was linearized and transformed into *K. lactis* competent cells. One liter of spent culture medium obtained from *K. lactis* cells secreting GLuc-KlCDB was mixed with a 20 ml bed volume of chitin beads for 1 h at RT. The chitin beads were poured into a column and subsequently washed with 10 column volumes (200 ml) of water. Bound protein was eluted with 20 mM NaOH. Four ml elution fraction were collected in tubes containing 1 ml 1M Tris-Cl pH 7.5 so as to neutralize the eluant as it came from the column. Twenty-five microliters of a one in forty dilution of each eluted fraction was assayed for luciferase activity, expressed as RLU (relative light units). FIG. 13 shows that active GLuc was eluted in fractions 2 to 10 with the highest activity found in fractions 3, 4 and 5.

What is claimed is:

1. A method of obtaining a concentrated preparation of a secreted recombinant protein, comprising:
   (a) transforming host expression cells with a vector containing a DNA, the DNA encoding a fusion protein comprising a chitin-binding domain (CBD) and a target protein;
   (b) expressing the fusion protein in the host expression cells in a fermentation medium and secreting the fusion protein therefrom;
   (c) binding the secreted fusion protein to a preparation of chitin magnetic beads in the fermentation medium of step (b) by means of the CBD, and
   (d) optionally removing the fusion protein from the chitin beads to obtain a concentrated preparation of the secreted recombinant protein.

2. A method according to claim 1, wherein (c) further comprises separating the chitin magnetic beads from the fermentation medium.

3. A method according to claim 1, wherein the host expression cells are chitinase-deficient cells.

4. A method according to claim 1, wherein the host expression cells are yeast cells.

5. A method according to claim 1, wherein the yeast cells are a single species selected from a *Kluyveromyces*, a *Yarrowia*, a *Pichia*, a *Hansenula*, and a *Saccharomyces* species.

6. A method according to claim 5, wherein the host expression cells are *Kluyveromyces*.

7. A method according to claim 6, wherein the *Kluyveromyces* is a *Kluyveromyces marxianus* variety *fragilis* or *lactis*.

8. A method according to claim 1, wherein the chitin magnetic beads are sterile.

9. A method according to claim 1, wherein the chitin is added to the mixture after cultivation.

10. A method according to claim 1, wherein the chitin magnetic beads are in a form of porous beads.

11. A method according to claim 1, wherein the chitin magnetic beads are in a form of non-porous beads.

12. A method according to claim 1, wherein recovering the fusion protein bound to the chitin in (d) further comprises applying a magnetic force.

13. A method according to claim 1, wherein the binding of the fusion protein to the chitin magnetic beads in (c) is reversible such that the fusion protein can be released from the chitin under non-denaturing conditions that differ from the conditions for binding.

* * * * *